(12) United States Patent
Bam et al.

(10) Patent No.: US 7,311,902 B2
(45) Date of Patent: Dec. 25, 2007

(54) CONJUGATES COMPRISING HUMAN IL-18 AND SUBSTITUTION MUTANTS THEREOF

(75) Inventors: Narendra Bam, King of Prussia, PA (US); Jacob Bongers, King of Prussia, PA (US); Robert B. Kirkpatrick, King of Prussia, PA (US); Cheryl A. Janson, Hinsdale, IL (US); Zdenka Jonak, King of Prussia, PA (US); Xianyang Qiu, Mystic, CT (US); Ping Yeh, King of Prussia, PA (US); Kyung Johanson, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 221 days.

(21) Appl. No.: 10/823,964

(22) Filed: Apr. 14, 2004

(65) Prior Publication Data
US 2005/0008615 A1 Jan. 13, 2005

Related U.S. Application Data

(60) Provisional application No. 60/462,947, filed on Apr. 15, 2003.

(51) Int. Cl.
C07K 14/54 (2006.01)
A61K 38/20 (2006.01)
(52) U.S. Cl. .................... 424/85.2; 530/351
(58) Field of Classification Search ............ None
See application file for complete search history.

(56) References Cited

U.S. PATENT DOCUMENTS

| | | | |
|---|---|---|---|
| 6,274,552 B1 * | 8/2001 | Tamarkin et al. ............. | 514/12 |
| 6,602,498 B2 | 8/2003 | Shen ...................... | 424/78.08 |
| 6,753,165 B1 * | 6/2004 | Cox et al. ................ | 435/69.51 |
| 2003/0171284 A1 | 9/2003 | Cox et al. ..................... | 514/12 |
| 2003/0191056 A1 | 10/2003 | Walker et al. ................ | 514/12 |
| 2003/0195154 A1 | 10/2003 | Walker et al. ................ | 514/12 |
| 2003/0232032 A1 * | 12/2003 | Janson et al. ............. | 424/85.2 |
| 2004/0062746 A1 * | 4/2004 | Martinez et al. ......... | 424/78.38 |
| 2004/0136992 A1 * | 7/2004 | Burton et al. ............ | 424/145.1 |

FOREIGN PATENT DOCUMENTS

| | | |
|---|---|---|
| EP | 0692536 | 1/1996 |
| EP | 0712931 | 5/1996 |
| EP | 0767178 | 4/1997 |
| EP | 0816499 | 1/1998 |
| EP | 0819757 | 1/1998 |
| EP | 0821005 | 1/1998 |
| EP | 0845530 | 6/1998 |
| EP | 0845530 A3 * | 6/1998 |
| EP | 0859052 | 8/1998 |
| EP | 110969 A1 | 6/2001 |
| EP | 0974600 | 9/2001 |
| WO | WO99/03887 | 1/1999 |
| WO | WO 99/45026 | 9/1999 |
| WO | WO 9945026 A1 * | 9/1999 |
| WO | WO00/42175 | 7/2000 |
| WO | WO01/03737 | 1/2001 |
| WO | WO01/62827 | 8/2001 |
| WO | WO01/87925 | 11/2001 |
| WO | WO02/077218 | 10/2002 |

OTHER PUBLICATIONS

Pettit et al., J Biol Chem. 1997;272(4):2312-2318.*
Kirkpatrick et al., Protein Expr Purif. Feb. 2003;27(2):279-92.*
Fu et al., Acta Biochimica et Biophysica Sinica. 2001; 33(4):368-372.*
Kim et al., J Biol Chem. Mar. 29, 2002; 277(13):10998-11003.*
Katre et al., PNAS USA. 1987;84:1487-1491.*
Benjamin et al., Ann Rev Immune. 1984;2:67-101.*
Pomroy, et al., "Solubilization of Hydrophobic Peptides by Reversible Cysteine PEGylation," *Biochemical and Biophysical Research Communications*, 245: 618-621 (1998).
Albrecht, et al., "Production of Soluble ScFVS with C-Terminal-Free Thiol for Site-Specific Conjugation or Stable Dimeric ScFvs on Demand," *Bioconjugate Chem.*, 15: 16-26 (2004).
Sato, et al., "Transglutaminase-Mediated Dual and Site-Specific Incorporation of Poly(ethyleneglycol) Derivatives into a Chimeric Interleukin-2," *Bioconjugate Chem.*, 11: 502-509 (2000).
Manjula, et al, "Site-Specific PEGylation of Hemogobin at Cys-93(β): Correlation between the Colligative Properties of the PEGylated Protein and the Length of the Conjugated PEG Chain," *Bioconjugate Chem.*, 14: 464-472 (2003).
Pettit, et al., "Structure-Function Studies of Interleukin 15 using Site-specific Mutagenesis, Polyethylene Glycol Conjugation, and Homology Modeling," *The Journal of Biological Chemistry*, 272 (4): 2312-2318 (1997).
Yang, et al. , "Tailoring structure-function and pharmacokinetic properties of single-chain Fv proteins by site-specific PEGylation," *Protein Engineering*, 16(10): 761-770 (2003).
Uchio, et al., "Site-specific insulin conjugates with enhanced stability and extended action profile," *Advanced Drug Delivery Reviews*, 35: 289-306 (1999).
Stimmel, et al., "Site-specific Conjugation on Serine→Cysteine Variant Monoclonal Antibodies," *The Journal of Biological Chemistry*, 275 (39): 30445-30450 (2000).

(Continued)

Primary Examiner—Gary B. Nickol
Assistant Examiner—Cherie Woodward
(74) Attorney, Agent, or Firm—Elizabeth J. Hecht; Edward R. Gimmi; Sherry M. Knowles

(57) ABSTRACT

Human interleukin-18 (IL-18) polypeptides and substitution mutants thereof were conjugated to water-soluble polymers at specific sites on the human IL-18 protein. These conjugated human IL-18 and substitution mutants thereof retain biological activity. These conjugated cytokines demonstrate enhanced and unexpected biological properties when compared to the corresponding unconjugated cytokines.

34 Claims, 15 Drawing Sheets

OTHER PUBLICATIONS

Lee, et al., "Prolonged Circulating Lives of Single-Chain Fv Proteins Conjugated with Polyethylene Glycol: A Comparison of Conjugation Chemistries and Compounds," *Bioconjugate Chem.*, 10: 973-981 (1999).

Cantin, et al., "Polyethylene Glycol Conjugation at $Cys^{232}$ Prolongs the Half-Life of α1 Proteinase Inhibitor," *American Journal of Respiratory Cell Molecular Biology*, 27: 659-665 (2002).

Andrew P. Chapman, "PEGylated antibodies and antibody fragments for improved therapy: a review," *Advanced Drug Delivery Reviews*, 54: 531-545 (2002).

Yoshioka, et al., "Optimal site-specific PEGylation of mutant RNF-α improves its antitumor potency," *Biochemical and Biophysical Research Communications*, 315: 808-814 (2004).

Lee, et al., "N-Terminal Site-Specific Mono-PEGylation of Epidermal Growth Factor," *Pharmaceutical Research*, 20 (5): 818-825 (2003).

Clark, et al., "Long-acting Growth Hormones Produced by Conjugation with Polyethylene Glycol," *The Journal of Biological Chemistry*, 271 (36): 21969-21977 (1996).

Haruya Sato, "Enzymatic procedure for site-specific pegylation of proteins," *Advanced Drug Delivery Reviews*, 54: 487-504 (2002).

Hinds, et al., "Effects of PEG conjugation on insulin properties," *Advanced Drug Delivery Reviews*, 54: 505-530 (2002).

Leong, et al., "Adapting Pharmacokinetic Properties of a Humanized Anti-Interleukin-8 Antibody for Therapeutic Applications Using Site-Specific Pegylation," *Cytokine*, 16 (3):106-119 (2001).

Seely, et al., "Issues encountered in the production of site-specific mono-PEGylated therapeutic proteins," *Polymer Preprints (American Chemical Society, Division of Polymer Chemistry)*, 38(1): 572-573 (1997).

Zalipsky, et al., "Reversible PEGylation: thiolytic regeneration of active protein from its polymer conjugates," *Peptides: The Wave of the Future, Proceedings of the Second International and the Seventeenth American Peptide Symposium*, San Diego, CA, Jun. 9-14, 2001, pp. 953-954.

Benjamin, et al., "The Antigenic Structure of Proteins: A Reappraisal," *Ann. Rev. Immunol.*, 1984, vol. 2, pp. 67-101.

Francis, et al., "PEGylation of Cytokines and Other Therapeutic Proteins and Peptides: The Importance of Biological Optimisation of Coupling Techniques," *International Journal of Hematology*, 1998, vol. 68, pp. 1-18.

Katre, et al., "Chemical Modification of Recombinant Interleukin 2 by Polyethylene Glycol Increases its Potency in the Murine Meth A Sarcoma Model," *Proc. Natl. Acad. Sci.*, 1987, vol. 84, pp. 1487-1491.

Kim, et al., "Identification of Amino Acid Residues Critical for Biological Activity in Human Interleukin-18," *The Journal of Biological Chemistry*, 2002, vol. 277, No. 13, pp. 10998-11003.

Kirkpatrick, et al., "A bicistronic Expression System for Bacterial Production of Authentic Human Interleukin-18," *Protein Expression and Purification*, 2003, vol. 27, pp. 279-292.

Yi, et al. ,"$Asp^{126}$, $Asp^{130}$ and $Asp^{134}$ are Necessary for Human IL-18 to Elicit IFN-γ Production from PBMC," *Acta Biochimica et Biophysica Sinica*, 2001, vol. 33, No. 4, pp. 368-372.

\* cited by examiner

Figure 1

YFGKL ESKLS VIRNL NDQVL FIDQG NRPLF EDMTD SDCRD NAPRT IFIIS    50
MYKDS QPRGM AVTIS VKCEK ISTLS CENKI ISFKE MNPPD NIKDT KSDII   100
FFQRS VPGHD NKMQF ESSSY EGYFL ACEKE RDLFK LILKK EDELG DRSIM   150
FTVQN ED    157

Figure 2

```
NFGRL HCTTA VIRNI NDQVL FVDKR QPVFE DMTDI DQSAS EPQTR LIIYM   50
YKDSE VRGLA VTLSV KDSKM STLSC KNKII SFEEM DPPEN IDDIQ SDLIF  100
FQKRV PGHNK MEFES SLYEG HFLAC QKEDD AFKLI LKKKD ENGDK SVMFT  150
LTNLH QS    157
```

Figure 3

```
MHHHH HHTRG MAAEP VEDNC INFVA MKFID NTLYF IAEDD ENLES DYFGK  50
LESKL SVIRN LNDQV LFIDQ GNRPL FEDMT DSDCR DNAPR TIFII SMYKD 100
SQPRG MAVTI SVKCE KISTL SCENK IISFK EMNPP DNIKD TKSDI IFFQR 150
SVPGH DNKMQ FESSS YEGYF LACEK ERDLF KLILK KEDEL GDRSI MFTVQ 200
NED   203
```

Figure 4

```
YFGKL ESKLS VIRNL NDQVL FIDQG NRPLF EDMTD SDSRD NAPRT IFIIS   50
MYKDS QPRGM AVTIS VKCEK ISTLS CENKI ISFKE MNPPD NIKDT KSDII  100
FFQRS VPGHD NKMQF ESSSY EGYFL ACEKE RDLFK LILKK EDELG DRSIM  150
FTVQN ED    157
```

Figure 5

```
YFGKL ESKLS VIRNL NDQVL FIDQG NRPLF EDMTD SDSRD NAPRT IFIIS   50
MYKDS QPRGM AVTIS VKDEK ISTLS CECKI ISFKE MNPPD NIKDT KSDII  100
FFQRS VPGHD NKMQF ESSSY EGYFL ACEKE RDLFK LILKK EDELG DRSIM  150
FTVQN ED    157
```

Figure 6

```
YFGKL ESKLS VIRNL NDQVL FIDQG NRPLF EDMTD SDSRD NAPRT IFIIS    50
MYKDS QPRGM AVTIS VKDEK ISTLS CENKI ISFKE MNPPD NIKDT KSDII   100
FFQRS VPGHD NKMQF ESSSY CGYFL ACEKE RDLFK LILKK EDELG DRSIM   150
FTVQN ED    157
```

Figure 7

```
YFGKL ESKLS VIRNL NDQVL FIDQG NRPLF EDMTD SDSRD NAPRT IFIIS   50
MYKDS QPRGM AVTIS VKDEK ISTLS CENKI ISFKE MNPPD NIKDT KSDII  100
FFQRS VPGHD NKMQF ESSSY EGYFL ACEKE RDLFK LILKK EDECG DRSIM  150
FTVQN ED    157
```

Figure 8

```
YFGKL ESKLS VIRNL NDQVL FIDQG NRPLF EDMTD SDSRD NAPRT IFIIS    50
MYKDS QPRGM AVTIS VKDEK ISTLS CENKI ISFKE MNPPD NIKDT KSDII   100
FFQRS VPGHD NKMQF ESSSY EGYFL ACEKE RDLFK LILKK EDELG DRSIM   150
FTVQN EC    157
```

Figure 9

```
YFGKL ESKLS VIRNL NDQVL FIDQG NRPLF EDMTD SDSRD NAPRT IFIIS    50
MYKDS QPRGM AVTIS VKSEK ISTLS CENKI ISFKE MNPPD NIKDT KSDII   100
FFQRS VPGHD NKMQF ESSSY EGYFL ACEKE RDLFK LILKK EDECG DRSIM   150
FTVQN ED    157
```

Figure 10

YFGKL ESKLS VIRNL NDQVL FIDQG NRPLF EDMTD SDSRD NAPRT IFIIS    50
MYKDS QPRGM AVTIS VKSEK ISTLS CENKI ISFKE MNPPD NIKDT KSDII   100
FFQRS VPGHD NKMQF ESSSY EGYFL ACEKE RDLFK LILKK EDELG DRSIM   150
FTVQN EC    157

SEQUENCE LISTING

<160> NUMBER OF SEQ ID NOS: 28

<210> SEQ ID NO 1
<211> LENGTH: 157
<212> TYPE: PRT
<213> ORGANISM: Homo sapiens

<400> SEQUENCE: 1

```
Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 2
<211> LENGTH: 157
<212> TYPE: PRT
<213> ORGANISM: Mus musculus

<400> SEQUENCE: 2

```
Asn Phe Gly Arg Leu His Cys Thr Thr Ala Val Ile Arg Asn Ile Asn
 1               5                  10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Asp Glu Asn Gly Asp
    130                 135                 140

Lys Ser Val Met Phe Thr Leu Thr Asn Leu His Gln Ser
145                 150                 155
```

```
<210> SEQ ID NO 3
<211> LENGTH: 203
<212> TYPE: PRT
<213> ORGANISM: Homo sapiens

<400> SEQUENCE: 3

Met His His His His His Thr Arg Gly Met Ala Ala Glu Pro Val
 1               5                  10                  15

Glu Asp Asn Cys Ile Asn Phe Val Ala Met Lys Phe Ile Asp Asn Thr
                 20                  25                  30

Leu Tyr Phe Ile Ala Glu Asp Glu Asn Leu Glu Ser Asp Tyr Phe
             35                  40                  45

Gly Lys Leu Glu Ser Lys Leu Ser Val Ile Arg Asn Leu Asn Asp Gln
 50                  55                  60

Val Leu Phe Ile Asp Gln Gly Asn Arg Pro Leu Phe Glu Asp Met Thr
 65                  70                  75                  80

Asp Ser Asp Cys Arg Asp Asn Ala Pro Arg Thr Ile Phe Ile Ile Ser
                 85                  90                  95

Met Tyr Lys Asp Ser Gln Pro Arg Gly Met Ala Val Thr Ile Ser Val
                100                 105                 110

Lys Cys Glu Lys Ile Ser Thr Leu Ser Cys Glu Asn Lys Ile Ile Ser
                115                 120                 125

Phe Lys Glu Met Asn Pro Pro Asp Asn Ile Lys Asp Thr Lys Ser Asp
                130                 135                 140

Ile Ile Phe Phe Gln Arg Ser Val Pro Gly His Asp Asn Lys Met Gln
145                 150                 155                 160

Phe Glu Ser Ser Ser Tyr Glu Gly Tyr Phe Leu Ala Cys Glu Lys Glu
                165                 170                 175

Arg Asp Leu Phe Lys Leu Ile Leu Lys Lys Glu Asp Glu Leu Gly Asp
                180                 185                 190

Arg Ser Ile Met Phe Thr Val Gln Asn Glu Asp
            195                 200

<210> SEQ ID NO 4
<211> LENGTH: 157
<212> TYPE: PRT
<213> ORGANISM: Homo sapiens
<220> FEATURE:
223> OTHER INFORMATION: Whereby the Cysteine at position 38 of this
     human IL-18 sequence has been replaced with Serine.

<400> SEQUENCE: 4

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
                 20                  25                  30

Met Thr Asp Ser Asp Ser Arg Asp Asn Ala Pro Arg Thr Ile Phe Ile
             35                  40                  45

Ile Ser Met Tyr Lys Asp Ser Gln Pro Arg Gly Met Ala Val Thr Ile
 50                  55                  60

Ser Val Lys Cys Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110
```

```
Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155

<210> SEQ ID NO 5
<211> LENGTH: 157
<212> TYPE: PRT
<213> ORGANISM: Homo sapiens
<220> FEATURE:
<223> OTHER INFORMATION: Whereby the Cysteine at position 38 of this
      human IL-18 sequence has been replaced with Serine, the Cysteine
      at position 68 has been replaced with Aspartic acid, and the
      Asparagine at position 78 has been replaced with Cysteine.

<400> SEQUENCE: 5

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Asp Glu Lys Ile Ser Thr Leu Ser Cys Glu Cys Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155

<210> SEQ ID NO 6
<211> LENGTH: 157
<212> TYPE: PRT
<213> ORGANISM: Homo sapiens
<220> FEATURE:
<223> OTHER INFORMATION: Whereby the Cysteine at position 38 of this
      human IL-18 sequence has been replaced with Serine, the Cysteine
      at position 68 has been replaced with Aspartic acid, and the
      Glutamic acid at position 121 has been replaced with Cysteine.

<400> SEQUENCE: 6

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Asp Glu Lys Ile Ser Thr Leu Ser Cys Glu Asn Lys Ile
```

```
                65                  70                  75                  80
Ile Ser Phe Lys Glu Met Asn Pro Pro Asp Asn Ile Lys Asp Thr Lys
                    85                  90                  95

Ser Asp Ile Ile Phe Phe Gln Arg Ser Val Pro Gly His Asp Asn Lys
            100                 105                 110

Met Gln Phe Glu Ser Ser Ser Tyr Cys Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 7
<211> LENGTH: 157
<212> TYPE: PRT
<213> ORGANISM: Homo sapeins
<220> FEATURE:
<223> OTHER INFORMATION: Whereby the Cysteine at position 38 of this
      human IL-18 sequence has been replaced with Serine, the Cysteine
      at position 68 has been replaced with Aspartic acid, and the
      Leucine at position 144 has been replaced with Cysteine.

<400> SEQUENCE: 7

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Asp Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Cys
    130                 135                 140

Gly Asp Arg Ser Ile Met Phe Thr Val Gln Asn Glu Asp
145                 150                 155

<210> SEQ ID NO 8
<211> LENGTH: 157
<212> TYPE: PRT
<213> ORGANISM: Homo sapiens
<220> FEATURE:
<223> OTHER INFORMATION: Whereby the Cysteine at position 38 of the
      human IL-18 sequence has been replaced with Serine, the Cysteine
      at position 68 has been replaced with Aspartic acid, and Aspartic
      acid at position 157 has been replaced with Cysteine.

<400> SEQUENCE: 8

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30
```

```
Met Thr Asp Ser Asp Ser Arg Asp Asn Ala Pro Arg Thr Ile Phe Ile
            35                  40                  45

Ile Ser Met Tyr Lys Asp Ser Gln Pro Arg Gly Met Ala Val Thr Ile
     50                  55                  60

Ser Val Lys Asp Glu Lys Ile Ser Thr Leu Ser Cys Glu Asn Lys Ile
65                   70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
            130                 135                 140

Gly Asp Arg Ser Ile Met Phe Thr Val Gln Asn Glu Cys
145                 150                 155
```

<210> SEQ ID NO 9
<211> LENGTH: 157
<212> TYPE: PRT
<213> ORGANISM: Homo sapeins
<220> FEATURE:
<223> OTHER INFORMATION: Whereby the Cysteine at position 38 of the
      human IL-18 sequence has been replaced with Serine, the Cysteine
      at position 68 has been replaced with Serine, and Leucine at
      position 144 has been replaced with Cysteine.

<400> SEQUENCE: 9

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
            35                  40                  45

Ile Ser Met Tyr Lys Asp Ser Gln Pro Arg Gly Met Ala Val Thr Ile
     50                  55                  60

Ser Val Lys Ser Glu Lys Ile Ser Thr Leu Ser Cys Glu Asn Lys Ile
65                   70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Cys
            130                 135                 140

Gly Asp Arg Ser Ile Met Phe Thr Val Gln Asn Glu Asp
145                 150                 155
```

<210> SEQ ID NO 10
<211> LENGTH: 157
<212> TYPE: PRT
<213> ORGANISM: Homo sapiens
<220> FEATURE:
<223> OTHER INFORMATION: Whereby the Cysteine at position 38 of the
      human IL-18 sequence has been replaced with Serine, the Cysteine
      at position 68 has been replaced with Serine, and Aspartic acid at
      position 157 has been replaced with Cysteine.

<400> SEQUENCE: 10

```
Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
             20                  25                  30

Met Thr Asp Ser Asp Ser Arg Asp Asn Ala Pro Arg Thr Ile Phe Ile
         35                  40                  45

Ile Ser Met Tyr Lys Asp Ser Gln Pro Arg Gly Met Ala Val Thr Ile
     50                  55                  60

Ser Val Lys Ser Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
             85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Cys
145                 150                 155

<210> SEQ ID NO 11
<211> LENGTH: 4
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 11

Tyr Phe Gly Lys
 1

<210> SEQ ID NO 12
<211> LENGTH: 4
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 12

Leu Glu Ser Lys
 1

<210> SEQ ID NO 13
<211> LENGTH: 5
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 13

Leu Ser Val Ile Arg
 1               5

<210> SEQ ID NO 14
<211> LENGTH: 26
<212> TYPE: PRT
<213> ORGANISM: Artificial Sequence
<220> FEATURE:
```

```
<223> OTHER INFORMATION: Tryptic peptides predicted for
      S-carboxymethylated wild type IL-18

<400> SEQUENCE: 14

Asn Leu Asn Asp Gln Val Leu Phe Ile Asp Gln Gly Asn Arg Pro Leu
 1               5                  10                  15

Phe Glu Asp Met Thr Asp Ser Asp Cys Arg
             20                  25

<210> SEQ ID NO 15
<211> LENGTH: 5
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 15

Asp Asn Ala Pro Arg
 1               5

<210> SEQ ID NO 16
<211> LENGTH: 9
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 16

Thr Ile Phe Ile Ile Ser Met Tyr Lys
 1               5

<210> SEQ ID NO 17
<211> LENGTH: 5
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 17

Asp Ser Gln Pro Arg
 1               5

<210> SEQ ID NO 18
<211> LENGTH: 9
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 18

Gly Met Ala Val Thr Ile Ser Val Lys
 1               5

<210> SEQ ID NO 19
<211> LENGTH: 9
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 19

Ile Ser Thr Leu Ser Cys Glu Asn Lys
```

-continued

```
1               5

<210> SEQ ID NO 20
<211> LENGTH: 5
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 20

Ile Ile Ser Phe Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 21

Glu Met Asn Pro Pro Asp Asn Ile Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 22

Ser Asp Ile Ile Phe Phe Gln Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 23

Ser Val Pro Gly His Asp Asn Lys
1               5

<210> SEQ ID NO 24
<211> LENGTH: 17
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 24

Met Gln Phe Glu Ser Ser Ser Tyr Glu Gly Tyr Phe Leu Ala Cys Glu
1               5                   10                  15

Lys

<210> SEQ ID NO 25
<211> LENGTH: 4
<212> TYPE: PRT
<213> ORGANISM: Artificial Sequence
```

```
<220> FEATURE:
<223> OTHER INFORMATION: Tryptic peptides predicted for
      S-carboxymethylated wild type IL-18

<400> SEQUENCE: 25

Asp Leu Phe Lys
 1

<210> SEQ ID NO 26
<211> LENGTH: 4
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 26

Leu Ile Leu Lys
 1

<210> SEQ ID NO 27
<211> LENGTH: 7
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 27

Glu Asp Glu Leu Gly Asp Arg
 1               5

<210> SEQ ID NO 28
<211> LENGTH: 10
<212> TYPE: PRT
<213> ORGANISM: Artificial Sequence
<220> FEATURE:
<223> OTHER INFORMATION: Tryptic peptides predicted for
      S-carboxymethylated wild type IL-18

<400> SEQUENCE: 28

Ser Ile Met Phe Thr Val Gln Asn Glu Asp
 1               5                  10
```

CONJUGATES COMPRISING HUMAN IL-18 AND SUBSTITUTION MUTANTS THEREOF

CROSS-REFERENCE TO RELATED APPLICATIONS

This application claims benefit to the earlier provisional U.S. Application No. 60/462,947, filed on Apr. 15, 2003, the contents of which are incorporated herein by reference in their entirety.

FIELD OF THE INVENTION

The instant invention relates to the field of site-specific protein conjugation. More specifically, the instant invention pertains to conjugation of water-soluble polymers to human interleukin-18 (herein "IL-18") polypeptides, substitution mutants thereof, and fragments thereof.

BACKGROUND OF THE INVENTION

Covalent attachment of biologically active compounds to water-soluble polymers is one method for alteration and control of biodistribution, pharmacokinetics, and often, toxicity for these compounds (Duncan, R. and Kopecek, J. (1984) Adv. Polym. Sci. 57:53-101). Many water-soluble polymers have been used to achieve these effects, such as poly(sialic acid), dextran, poly(N-(2-hydroxypropyl)methacrylamide) (PHPMA), poly(N-vinylpyrrolidone) (PVP), poly(vinyl alcohol) (PVA), poly(ethylene glycol-co-propylene glycol), poly(N-acryloyl morpholine (PAcM), and poly(ethylene glycol) (PEG) (Powell, G. M. (1980) Polyethylene glycol. In R. L. Davidson (Ed.) HANDBOOK OF WATER SOLUBLE GUMS AND RESINS. McGraw-Hill, New York, chapter 18). PEG possess an ideal set of properties: very low toxicity (Pang, S. N. J. (1993) J. Am. Coll. Toxicol. 12: 429-456) excellent solubility in aqueous solution (Powell, supra), low immunogenicity and antigenicity (Dreborg, S. and Akerblom, E. B. (1990) Crit. Rev. Ther. Drug Carrier Syst. 6: 315-365). PEG-conjugated or "PEGylated" protein therapeutics, containing single or multiple chains of polyethylene glycol on the protein, have been described in the scientific literature (Clark, R., et al. (1996) J. Biol. Chem. 271: 21969-21977; Hershfield, M. S. (1997) Biochemistry and immunology of poly(ethylene glycol)-modified adenosine deaminase (PEG-ADA). In J. M. Harris and S. Zalipsky (Eds) Poly(ethylene glycol): Chemistry and Biological Applications. American Chemical Society, Washington, D.C., p145-154; Olson, K., et al. (1997) Preparation and characterization of poly(ethylene glycol)ylated human growth hormone antagonist. In J. M. Harris and S. Zalipsky (Eds) Poly(ethylene glycol): Chemistry and Biological Applications. American Chemical Society, Washington, D.C., p170-181).

Conjugated proteins have numerous advantages over their unmodified counterparts. For example, PEG-modification has extended the plasma half-life of many proteins (Francis, G. E., et al. (1992) PEG-modified proteins. In: STABILITY OF PROTEIN PHARMACEUTICALS: in vivo PATHWAYS OF DEGRADATION AND STRATEGIES FOR PROTEIN STABILIZATION (ed. by T. J. Ahern and M. Manning). Plenum Press, New York). The basis for this increase involves several factors. The increased size of the PEG-modified conjugate reduces the glomerular filtration when the 70 kD threshold is exceeded (Futertges, F. and Abuchowski, A. (1990) J. Controlled Release 11: 139-148). There is also reduced clearance by the reticuloendothelial system via both carbohydrate receptors and protein-receptor interactions (Beauchamp, C. O., et al. (1983) Anal. Biochem. 131: 25-33). Reduced proteolysis (Chiu, H. C., et al. (1994) J. Bioact. Comp. Polym. 9: 388-410) may also contribute to an enhanced half-life. Antigenicity and immunogenicity are also reduced (Nucci, M. L., et al. (1991) Adv. Drug Del. Rev. 6: 133-151), and this accounts for reduction in life-threatening reactions after repeated dosing. The combination of all these factors leads to increased bioavailability in vivo (Katre, N. V., et al. (1987) PNAS USA 84:1487-1491; Hershfield, M. S., et al. (1987) New England Journal of Medicine 316: 589-596), and this is potentially very important in the use of PEG-cytokine adducts as pharmacological agents. Dose can be reduced (to alleviate toxicity) and more convenient schedule of dosing can be developed.

IL-18 is a non-glycosylated monomer of 18 Kd with a primary structure most closely related to IL-1α of the IL-1 β-trefoil subfamily. Murine and human IL-18 cDNA encode a precursor protein consisting of 192 and 193 amino acids, respectively. The homology between human and murine IL-18 is 65%. Pro-IL-18 requires processing by caspases, such as ICE (caspase-1) or caspase-4, into bioactive mature protein (157 amino acids) in order to mediate biologic activity. The activity of IL-18 is mediated via an IL-18 receptor (IL-18R) complex (made up of a binding chain (IL-18Rα) and a signaling chain (IL-18Rβ)). The biological activities of IL-18 that support its therapeutic potential for tumor immunotherapy include induction and production of IFNγ· and GM-CSF, enhancement of NK cell cytolytic activity and promotion, and differentiation of naive T cells into Th1 cells. In response to IL-18, cytotoxic T lymphocytes (CTLs) and memory cells are generated that display potent anti-tumor activity. Other regulatory functions include up-regulation of functional Fas ligand (FasL) expression on NK and T cells (suggesting that the IL-18 anti-tumor activity is mediated in part by Fas-FasL interaction, inducing tumor apoptosis); activation of monocytes/macrophage, B cells, and anti-angiogenesis.

IL-18 binding protein (IL-18BP) is a naturally occurring soluble circulating protein that has been recently described as an antagonist of IL-18. IL-18BP bears no significant homology to either IL-18 receptor, in that it contains a single putative Ig domain that bears very limited homology to the third Ig domain of the type II IL-1 receptor. Much greater homology to IL-18BP can be found in a family of proteins encoded by several poxviruses (swinepox, cowpox, variola, molluscum, contagiosum, and ectromelia). Poxviruses encode decoy receptors of many cytokines and these receptors are instrumental in viral avoidance of immune responses. Because IL-18 is one of the early signals leading to IFNγ production by Th1 cells, blocking IL-18 activity by IL-18BP may be involved in down-regulating one of the earliest phases of the immune response. Elevated levels of IL-18BP could be detrimental to the effectiveness of recombinant IL-18 therapy.

As a single agent, a recombinant form of murine IL-18 stimulated the murine immune system, resulting in partial and complete tumor regressions and/or induction of immunological memory in various established tumor models. In combination with chemotherapeutic agents commonly used in the clinical setting, such as topotecan, murine IL-18 demonstrated a synergistic effect, resulting in improved efficacy at the local and/or systemic levels in various established tumor models. Potential biomarkers of IL-18 activity were investigated to correlate with early events of IL-18 mediated immune activation, together with extensive toxicology and pharmacokinetic studies of both murine IL-18 and human IL-18 recombinant forms of IL-18. These preclinical data support the clinical development of human IL-18 as a novel form of immunotherapy, or as an adjunct for cancer vaccines, or an adjuvant to cytotoxic agents and other biologicals, such as topotecan and IL-2 respectively, for the treatment of patients suffering from different types of cancers.

SUMMARY OF THE INVENTION

In one aspect, the instant invention pertains to a biologically active composition comprising an IL-18 polypeptide covalently conjugated to a water-soluble polymer, wherein the polypeptide is human IL-18, a substitution mutant thereof, or a fragment thereof.

In a second aspect, the instant invention pertains to methods of treating cancer in a patient by administering a therapeutically effective dose of a biologically active composition comprising an IL-18 polypeptide covalently conjugated to a water-soluble polymer, wherein the polypeptide is human IL-18 or a substitution mutant thereof. In another aspect, the invention pertains to such methods for the treatment of an immunosensitive tumor chosen from the group of: renal cell carcinoma, melanoma, other IL-18 responsive tumor types (e.g., myeloma and lymphoma), and melanoma.

In a third aspect, the instant invention pertains to a method of preparing a biologically active composition comprising the steps of:
  (a) obtaining a human IL-18 polypeptide or a substitution mutant thereof; and
  (b) contacting the polypeptide with a functionalized water-soluble polymer.

In a fourth aspect, the instant invention pertains to a method of improving the pharmacokinetics and pharmacodynamics of human IL-18 or a substitution mutant thereof, comprising the step of conjugating the human IL-18 or the substitution mutant to a water-soluble polymer.

In a fifth aspect, the instant invention pertains to a method of improving the subcutaneous bioavailability of human IL-18 or a substitution mutant thereof, comprising the step of conjugating the human IL-18 or the substitution mutant to a water-soluble polymer.

In a sixth aspect, the instant invention pertains to a method of reducing binding (interaction) of human IL-18 or a substitution mutant thereof, comprising the step of conjugating the human IL-18 or the substitution mutant to a water-soluble polymer to human IL-18 binding protein (IL-18BP).

BRIEF DESCRIPTION OF THE FIGURES

FIG. 1 shows the amino acid sequence of native human IL-18 (SEQ ID NO:1).

FIG. 2 shows the amino acid sequence of murine IL-18 (SEQ ID NO:2).

FIG. 3 shows the amino acid sequence of human His Pro IL-18 (SEQ ID NO:3).

FIG. 4 shows the amino acid sequence of the substitution mutant, human IL-18 C38S (SEQ ID NO:4).

FIG. 5 shows the amino acid sequence of the substitution mutant, human IL-18 C38S, C68D, N78C (SEQ ID NO:5).

FIG. 6 shows the amino acid sequence of the substitution mutant, human IL-18 C38S, C68D, E121C (SEQ ID NO:6).

FIG. 7 shows the amino acid sequence of the substitution mutant, human IL-18 C38S, C68D, L144C (SEQ ID NO:7).

FIG. 8 shows the amino acid sequence of the substitution mutant, human IL-18 C38S, C68D, D157C (SEQ ID NO:8).

FIG. 9 shows the amino acid sequence of the substitution mutant, human IL-18 C38S, C68S, L144C (SEQ ID NO:9).

FIG. 10 shows the amino acid sequence of the substitution mutant, human IL-18 C38S, C68S, D157C (SEQ ID NO:10).

DETAILED DESCRIPTION OF THE INVENTION

Figure 11:
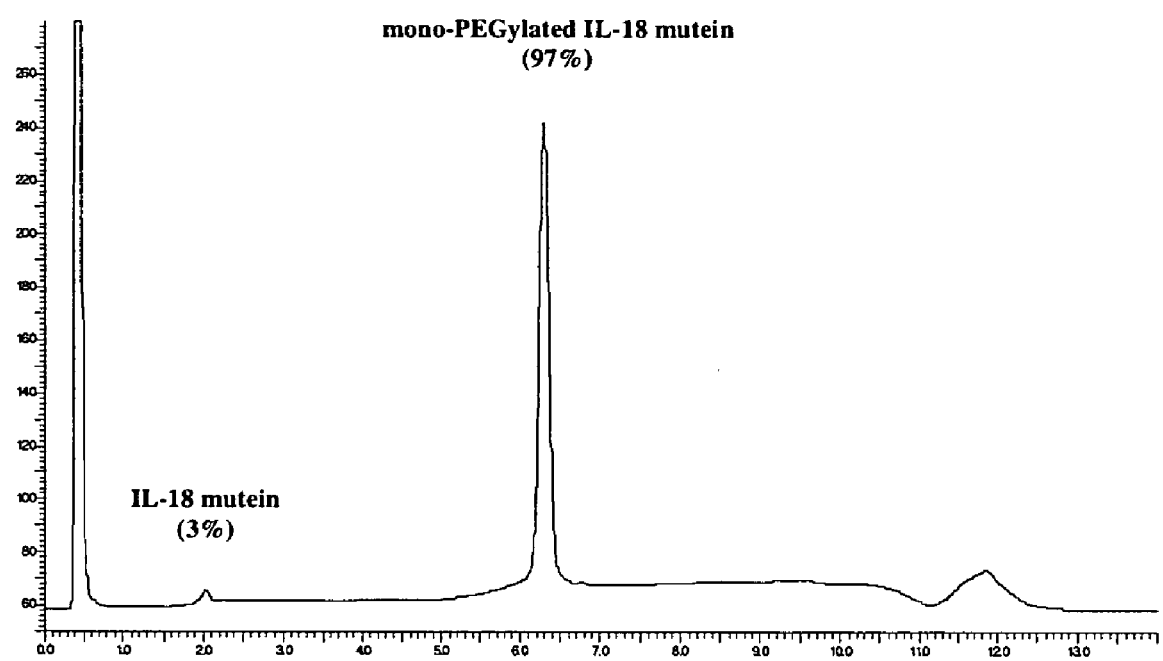
FIG. 11 shows a typical RP-HPLC chromatogram of reaction mixture following PEGylation of a human IL-18 substitution mutant (C38S, C68S, D157C) (SEQ ID NO: 10).

The present invention provides a composition comprising a human IL-18 polypeptide, wherein the polypeptide is conjugated to a water-soluble polymer. The instant conjugated polypeptide demonstrates unexpected biological properties, as compared to the corresponding unconjugated polypeptide.

Immunotherapy may represent a valuable addition to the oncology treatment armamentarium, with the potential to show an anti-tumor effect associated with decreased side effects and to improve patients' quality of life. Interleukin-18 (IL-18) is currently being studied as a new form of tumor immunotherapy for renal cell carcinoma and melanoma. Both these tumor types are considered immunosensitive and may respond to IL-18 as a single agent. The combination of IL-18 with cytotoxic drugs and other biologicals will expand the clinical use of IL-18 into different types of hematologic and solid tumors.

Pegylated IL-18 molecules are variants of IL-18 that may contain from one to five amino acid substitutions. These molecules have improved pharamacokinetics (PK), but most importantly, increased pharmacodynamic (PD) markers, as measured by induction and expression of different cytokines and soluble proteins. The term, "pharmacokinetics," as used herein, refers to the kinetics of drug absorption, distribution and elimination (i.e., metabolism and excretion). The term, "pharmacodynamics," as used herein, refers to the relationship between drug concentration at the site(s) of action (in the case of IL-18, the receptor) and the pharmacological response. Important PD markers include changes, such as an enhancement and/or increase in phenotypic profile of cells (e.g., lymphocytes) and cell-surface markers. Pegylated IL-18 molecules showed decreased capability to form complexes with IL-18 binding protein (IL-18BP). Prevention of complex formation with IL-18BP may have a benefit in clinic, because IL-18BP may be a potential inhibitor of IL-18 activity. Bufler, et al., *PNAS*, 99(21):13723-13728 (2002). Pegylated IL-18 molecules may be administered with reduced frequency of dosing that could be of great benefit in combination therapies with other biologicals, vaccines or cytotoxic agents. Most importantly, pegylation could reduce or eliminate immunogenicity in treated patients.

Some examples of the above mentioned benefits are presented below in Examples 7, 8, 9 and 10. The IL-18 substitution mutant that contains 3 mutations (C38S, C68S, D157C) (SEQ ID NO: 10) and a single site-specific 20K PEG covalently linked to the C-terminal cysteine residue (C157 position), showed improved PK, but most importantly, increased PD markers as measured by induction and expression of CD64 and neopterin in Cynomolgus monkeys and induction of IFNγ in mice. Example of reduced frequency of dosing with equal anti-tumor efficacy and retained immunological memory was done in murine tumor model MOPC-315 by using murine pegylated IL-18 (data not shown).

Other modified polypeptides that are useful in the instant invention are variants or fragments of these proteins that share the biological activity of the mature (i.e., unmodified) human IL-18 protein. As defined herein, such variants include modified proteins also characterized by alterations made in the known amino sequence of the proteins. Such variants are characterized by having an amino acid sequence differing from that of the mature protein by eight or fewer amino acid residues, and, preferably, by about five or fewer residues. In one embodiment of the invention, any differences in the amino acid sequences of the proteins involve only conservative amino acid substitutions. Conservative amino acid substitutions occur when an amino acid has substantially the same charge as the amino acid for which it is substituted and the substitution has no significant effect on the local conformation of the protein or its biological activity. Alternatively, changes such as the introduction of a certain amino acid in the sequence which may alter the stability of the protein, or permit it to be expressed in a desired host cell, may be preferred. Moreover, variation in primary amino acid sequence with no substantial change in protein structure and function are known in this art. Such variants are readily detected and predicted by algorithms used by those skilled in this art. For example, the well known BLAST algorithm (Altschul, S. F., et al. (1990) *J. Mol. Biol.* 215:403-410) utilizes an amino acid substitution matrix to predict and evaluate tolerable amino acid substitution at residues of the query sequence. Accordingly, the skilled artisan appreciates the scope and meaning of the term "variant" when used to describe equivalent embodiments of a given polypeptide sequence. The term, "substitution mutant," as used herein, means a protein in which an amino acid residue is replaced with another amino acid residue. A human IL-18 "substitution mutant," as used herein, means a mutant that comprises from one to five amino acid substitutions in the sequence of SEQ ID NO:1, said substitutions being at an amino acid residue chosen from the group of: the cysteine at residue 38, the cysteine at residue 68, the cysteine at residue 76, the asparagine at residue 78, the glutamic acid at residue 121, the cysteine at residue 127, the leucine at residue 144, and the aspartic acid at residue 157.

Cysteine is, by far, the most chemically reactive of the twenty common amino acids. Cysteine residues play key roles in protein structure and function including disulfide bridging, active-site chemistry, metal ion coordination, nitric oxide (NO) binding, etc. Hence, cysteines are among the most strongly sequence-conserved amino acids in the genome. Human IL-18 contains four cysteine sulfhydryls with no obvious structural or other biological functions. Cysteines 38 and 68 are solvent-exposed on the surface of the IL-18 molecule as shown by many experimental observations. These observations include: mixed-disulfide adducts with 2-mercaptoethanol during purification (but not dithiothreitol, of course), highly selective biotinylations and PEGylations of these two cysteines, and their tendency to undergo air oxidation and form a 38-to-68 intramolecular disulfide bridge in addition to intermolecular disulfide bridged "dimers" at higher concentrations of IL-18. These disulfide bridging reactions can be accelerated by pyridyl disulfide, glutathione, and other thiol-disulfide exchange catalysts. Cysteines 76 and 127, on the other hand, are relatively chemically inert compared to cysteines 38 and 68. Thus cysteines 76 and 127 are not solvent-exposed but buried within the folded IL-18 molecule similar to the two buried cysteines in IL-1 beta and are located in sequence positions similar to other members of the IL-1 family (Kumar, et al., *J. Biol. Chem.*, 275: 10308 (2000); Smith, et al., *J. Biol. Chem.*, 275: 1169-1175 (2000)).

The dispositions and reactivities of the four cysteines in IL-18 bear a striking resemblance to the four cysteines in the β-trefoil cytokine, basic fibroblast growth factor (FGF-2). FGFs are a family of homologous heparin-binding protein mitogens that have been extensively studied and developed for wound healing and other therapeutic indications (Ortega, et al., *J. Biol. Chem.*, 266: 5842-5846 (1991); Tsai, et al., *Pharm. Res.*, 10: 649-659 (1993)). Both hIL-18 and hFGF-2 are β-trefoil proteins; both proteins contain two solvent-exposed and two buried cysteines; both have low melting temperatures just above physiological temperature (Tm=40-50oC) characteristic of many β-trefoils, and both proteins show rapid PD/PK clearance of activity. As noted by one investigator (Estape, et al., *Biochem. J.*, 335: 343-349 (1998), "hFGF-2 is known as a notoriously unstable protein." The in vivo half-life of FGF-1 is increased by as much as 10-fold by specific binding to heparin, a polyanionic sulfated polysaccharide. In addition to stabilizing FGF, heparin also plays a key role in the binding of FGF to the FGF receptor (Pellegrini, et al., *Nature*, 407: 1029-1034 (2000)). It is not known if the other β-trefoil cytokines have similar "stabilizing ligands," although Kobata and coworkers recently reported on specific binding interactions of IL-1 beta with sulfated polysaccharides (Tandai-Hiruma, et al., *J. Biol. Chem.*, 274: 459-4466 (1999)).

The cysteines in FGF have been extensively studied by crystallography and biophysical techniques for both the native FGF's and cysteine-to-serine muteins. Chemical modification of the two solvent-exposed cysteines in hFGF-2, or the replacement of these cysteines by serines via site-directed mutagenesis, eliminates intra- and intermolecular disulfide bridging and greatly increases the stability of FGF mitogenic activity (Seno, et al., *Biochem. Biophys. Res. Commun.*, 151: 701-708 (1988)). Recently, researchers have proposed that the cysteines in the FGFs are conserved in the sequence precisely in order to form disulfide bridges thereby irreversibly inactivating the protein and limiting the in vivo lifetimes of these potent cytokines (Culajay, et al., *Biochemistry*, 39: 7153-7158 (2000)). Culajay, et al., supra, describes preliminary in vitro data that suggests a similar built-in regulatory mechanism for IL-18 involving cysteine sulfhydryl chemistry.

Buffered hIL-18 solutions (0.10 M sodium phosphate, pH 7.0) show an initial accumulation of a 38-to-68 intramolecular disulfide bridged form of IL-18 followed by the appearance of a 38-to-68,76-127 doubly bridged form after standing overnight at room temperature and at 5° C. The data show an initial accumulation of a 38-to-68 intramolecular disulfide bridged form of IL-18 followed by the appearance of a 38-to-68,76-127 doubly bridged form. The initial time course of these air oxidation reactions is consistent with a sequential reaction of the type A→B→C, i.e., an initial accumulation of 38-to-68 bridged IL-18 followed by it's conversion to the 38-to-68,76-to-127 doubly-bridged IL-18. The disulfide pairings in the reaction products were determined by tryptic mapping and mass spectrometry of the isolated peaks. It is interesting that the initial 38-to-68 form is more stable at 5° C. than at room temperature. The accumulation of this intermediate product is much greater at 5° C., while rates of reduction of the IL-18 starting material are roughly equivalent at the two temperatures. Excluding possible influences of the ambient concentrations of dissolved oxygen at these two temperatures, the data indicate that the 38-to-68 bridged form is thermally unstable with respect to the doubly-bridged product. The products can be converted back to the starting material by dithiothreitol (DTT) reduction.

The instant polypeptide may also occur as a multimeric form of the mature and/or modified protein useful in this invention, e.g., a dimer, trimer, tetramer or other aggregated form. Such multimeric forms can be prepared by physical association, chemical synthesis or recombinant expression and can contain cytokines produced by a combination of synthetic and recombinant techniques as detailed below. Multimers may form naturally upon expression or may be constructed into such multiple forms. Multimeric cytokines may include multimers of the same modified cytokine. Another multimer may be formed by the aggregation of different modified proteins. Still another multimer is formed by the aggregation of a modified cytokine of this invention and a known, mature cytokine. Preferably, a dimer or multimer useful in the invention would contain at least one desamino cytokine protein and at least one other cytokine or other protein characterized by having the same type of biological activity. This other protein may be an additional desamino cytokine, or another known protein.

A modified cytokine that is useful in the instant invention is human IL-18 protein (SEQ ID NO: 1), a substitution mutant thereof, or a fragment thereof. The instant invention therefore provides a method of enhancing the biological activity of human IL-18. This method involves modifying a natively or recombinantly produced human IL-18 or IL-18 substitution mutant, as described herein, such that it is covalently bound to a water-soluble polymer. Alternatively, multimers of cytokine molecules may be conjugated to water-soluble polymers. These conjugates may further enhance the biological activity of the resulting composition.

The human IL-18, human IL-18 substitution mutants, and human IL-18 fragments that are useful in the instant invention may be prepared by any of several methods described below. These polypeptide moieties may be prepared by the solid phase peptide synthetic technique of Merrifield ((1964) *J. Am. Chem. Soc.* 85:2149). Alternatively, solution methods of peptide synthesis known to the art may be successfully employed. The methods of peptide synthesis generally set forth in J. M. Stewart and J. D. Young, "Solid Phase Peptide Synthesis", Pierce Chemical Company, Rockford, Ill. (1984) or M. Bodansky, Y. A. Klauser and M. A. Ondetti, "Peptide Synthesis", John Wiley & Sons, Inc., New York, N.Y. (1976) may be used to produce the peptides of this invention.

Modified human IL-18 polypeptides may be derived from mature IL-18 by enzymatic digestion of the mature IL-18 with a suitable enzyme (see, for example, Oravecz, T. et al. (1997) *J. Exp. Med.* 186:1865; Proost, P. et al. (1998) *FEBS Letters* 432:73; Shioda, T. et al. (1998) *PNAS USA* 95:6331; and Walter, R. et al. (1980) *Mol. Cell. Biochem.* 30:111). Moreover, modified amino acids may be incorporated into the growing polypeptide chain during peptide synthesis (M. Hershfield, M. et al. (1991) *PNAS* 88:7185-7189; Felix, A. M. (1997) In J. M. Harris and S. Zalipsky (Eds) Poly (ethylene glycol): Chemistry and Biological Applications. American Chemical Society, Washington, D.C., p218-238). These modified amino acid residues may be chosen so as to facilitate covalent conjugation of water-soluble polymers. Also, variant polypeptides may be synthesized wherein amino acid addition, substitution, or deletion are chosen to facilitate subsequent polymer conjugation. Such variant polypeptides may be prepared by chemical synthesis or by recombinant expression. For example, incorporation of additional cysteine residues (by either substitution for existing non-cysteine residues or adding to one or both termini) may be desirable in order to facilitate polymer coupling through the sulfhydryl groups (e.g., Kuan, C. T., et al. (1994) *J. Biol. Chem.* 269:7610-7616; Chilkoti, A., et al. (1994) *Bioconjugate Chem.* 5:504-507).

Preferably, human IL-18 polypeptides that are useful in this invention may be produced by other techniques known to those of skill in the art, for example, genetic engineering techniques. See, e.g., Sambrook et al., in MOLECULAR CLONING, A LABORATORY MANUAL, 2nd edition, Cold Spring Harbor Laboratory, Cold Spring Harbor, N.Y. (1989). Systems for cloning and expression of a selected protein in a desired microorganism or cell, including, e.g., *E. coli, Bacillus, Streptomyces*, mammalian, insect, and yeast cells, are known and available from private and public laboratories and depositories and from commercial vendors.

In one embodiment of the invention, the human IL-18 polypeptides of the invention are produced through direct recombinant expression of IL-18. For example, human IL-18 protein can be recombinantly expressed by inserting its DNA coding sequence into a conventional plasmid expression vector under the control of regulatory sequences capable of directing the replication and expression of the protein in a selected host cell. Rosenberg, A. H., Gene 56, 125-135 (1987).

For recombinant production, host cells can be genetically engineered to incorporate expression systems or portions thereof for IL-18 polypeptides useful in the instant invention. Introduction of polynucleotides encoding human IL-18 into host cells can be effected by methods described in many standard laboratory manuals, such as Davis, et al., BASIC METHODS IN MOLECULAR BIOLOGY (1986) and Sambrook, et al., in MOLECULAR CLONING, A LABORATORY MANUAL, 2nd edition, Cold Spring Harbor Laboratory, Cold Spring Harbor, N.Y. (1989). Such methods include, but are not limited to: calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook, et al., supra. Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If the polypeptide is secreted into the medium, the medium can be recovered in order to recover and purify the polypeptide. If produced intracellularly, the cells must first be lysed before the polypeptide is recovered.

Polypeptides useful in the instant invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Water-soluble polymers that are useful in the instant invention are substantially non-antigenic in order to avoid unwanted immune reactivity towards the composition of the instant invention. Such water-soluble polymers can include, but are not limited to: polyethylene glycol homopolymers, polyethylene glycol copolymers, polypropylene glycol homopolymers, poly(N-vinylpyrrolidone), poly(vinyl alcohol), poly(ethylene glycol-co-propylene glycol), poly(N-2-(hydroxypropyl)methacrylamide), poly(sialic acid), poly(N-acryloyl morpholine), and dextran. Suitable polymers may be of any molecular weight. In one embodiment of the invention, the polymers have an average molecular weight between about 1000 daltons and about 100,000 daltons. In an alternative embodiment of the invention, the water-soluble polymers have an average molecular weight between about 4000 daltons and about 40,000 daltons. In yet another embodiment of the invention, the molecular weight of the aforementioned functionalized polymers is a member chosen from the group of: about 20,000 daltons to about 30,000 daltons. In a further embodiment of the invention, the aforementioned functionalized polymer has a molecular weight of about 20,000 daltons.

These polymers may be unsubstituted or substituted at one end with an alkyl group. For example, compositions of the invention can be those wherein the water-soluble polymer is a polyethylene glycol homopolymer. Polymers suitable for use in the instant invention may be branched, unbranched, star-shaped, or linear. In one embodiment of the invention, such compositions comprise a linear polyethylene glycol homopolymer. In another embodiment of the invention, such compositions comprise a branched polyethylene glycol homopolymer. Polymers that may be suitable for use in the instant invention are disclosed in the following patents, patent applications and publications: U.S. Pat. Nos. 4,097,470 4,847,325, 5,037,883, 5,252,714, 5,580,853, 5,643,575, 5,672,662, 5,739,208, 5,747,446, 5,824,784, 5,846,951, 5,880,255, 5,919,455, 5,919,758, 5,932,462, 5,985,263, 5,951,974, 5,990,237 6,042,822, 6,046,30, 6,107, 272 and 6,113,906; World Patent Publication No. WO 92/16555; European Patent Publication Nos. EP 727,437, EP 727,438, EP 439,508 and EP 714,402; Zalipsky, S. (1995) *Bioconjugate Chem* 6:150-165; Gregoriadis, G., et al. (1999) *Pharma Sciences* 9:61-66, each of which is incorporated herein by reference. Moreover, derivatized or functionalized polymers that have been modified in order to facilitate conjugation to polypeptides and other biological substances are suitable for use in the instant invention. For example, modifications of the polymers in order to facilitate conjugation through free amino groups (such as epsilon amino group at lysine residues or a free amino group at the N-terminus), free sulfhydryl groups on cysteine residues, or carbohydrate moieties, are desirable. Useful polymers may also include monomethoxy derivatives of polyethylene glycol (mPEG). Functionalized polymers that can be used in the instant invention can include, but are not limited to: methoxy polyethylene glycol succinimidyl propionate; methoxy polyethylene glycol succinimidyl butanoate; succinimidyl ester of carboxymethylated methoxy polyethylene glycol; methoxy polyethylene glycol aldehyde; methoxy polyethylene glycol hydrazide, methoxy polyethylene glycol iodoacetamide; methoxy polyethylene glycol maleimide; and methoxy polyethylene glycol tresylate.

The human IL-18 proteins described above can be conjugated to the polymer via either: (1) free amine group(s), for example, one or two to minimize loss of biological activity, (2) free carboxyl group(s), for example, one of two to minimize loss of biological activity, (3) free histidine group(s), (4) free sulfhydryl group(s) or (5) free thioether group(s) that are either naturally present or genetically engineered into the cytokine molecule and remain free after refolding. The number of polymer molecules that have been conjugated to the protein can be determined by various methods, including, for example, SDS-PAGE gel or size-exclusion chromatography with appropriate molecular markers, matrix-assisted laser desorption and ionization mass spectrometry (MALDI-MS) (Bullock, J., et al. (1996) *Anal. Chem.* 68:3258-3264), capillary electrophoresis (Kemp, G. (1998) *Biotechnol. Appl. Biochem.* 27:9-17; Robert, M. J. and Harris, J. M. (1998) *J. Pharm. Sci.* 87:1440-1445). The site of polymer attachment can be determined via digesting the protein into small fragments by an enzyme (e.g., trypsin, Glu-C) and separating by reverse-phase liquid chromatography. A peptide map of the protein before and after the polymer modification would be compared, and fragment with altered elution times sequenced to determine the location(s) of polymer attachments. Alternatively, the polymer can be either fluorescently or radioactively labeled prior to coupling to determine how many moles of the labeled polymer are attached per mole of the protein.

The residue(s) to be conjugated may be: (1) free sulfhydryl groups on cysteine residues; (2) any free amine groups (e.g., epsilon amine group at lysine residue or a free amine group at the N-terminal); (3) free carboxyl groups (e.g., the free carboxl groups on aspartate and glutamate residues); (4) free imidazole group on histidine, and (5) free thioether groups on methionine that are normally present or genetically engineered into the protein.

The reaction conditions for effecting conjugation further include conducting the above attachment reactions at pH about 6-9, more preferably at pH 6-7 if the reactive group of the protein is a free thiol group on the cysteine or the thio ether group on the methionine. Using the above approach, the protein is conjugated via at least one terminal thiol-reactive group added to the polymer. These thiol-reactive groups include but are not limited to: haloacetyl, maleimide, pyridyl disulfide derivatives, aziridines, acryloyl derivatives, arylating agents. The amount of intact activated polymer employed is generally 1- to 10-fold excess of the activated polymer over the protein which is in either monomeric or multimeric (preferable dimeric) forms. Generally, the reaction process involves reacting the activated polymer with the protein in a 2 to 1 (polymer to protein) ratio. Typically, the reaction is carried out in a phosphate buffer pH 6.2, 100 mM NaCl, at 4° C. for from about 1 hour to about 10 hours. Following the conjugation, the desired conjugated protein is recovered and purified by liquid chromatography or the like.

The reaction conditions for effecting conjugation further include conducting the above attachment reactions at pH about 6-9, more preferably at pH 6.5-7.5, if the reactive group of the protein is a free amine group, and also to reduce the deamidation reaction which is known to occur at alkaline pH (greater than 7) at asparagine and glutamine residues. Using the above approach, the protein is conjugated via at least one terminal amine-reactive group added to the polymer. These amine-reactive groups include but are not limited to: isothiocyanates, isocyanates, acyl azides, N-hydroxysuccinimide (NHS) esters, benzotriazole, imidazole, sulfonyl chlorides, aldehydes, glyoxals, epoxides, carbonates, aryl halides, imidoesters, iodoacetamides, tresylates and anhydrides. The amount of intact activated polymer employed is generally 1- to 10-fold excess over the protein which is in either monomeric or multimeric (preferable dimeric) forms. Generally the reaction process involves reacting the activated polymer with the protein in a 2 to 1 (polymer to protein) ratio. Typically, the reaction is carried out in a phosphate buffer pH 7.0, 100 mM NaCl, at 4° C. for from about 1 hour to about 4 hours. Following the conjugation, the desired conjugated protein is recovered and purified by liquid chromatography or the like.

The reaction conditions for effecting conjugation further include conducting the above attachment reactions at pH about 3-9, more preferably are at pH 4-5, if the reactive group of the protein is a free carboxylate group. The carboxyl group on the protein is activated by activation agents such as carbodiimides (e.g., DCC or EDC) or carbonyldiimidazole (e.g., CDI). Using the above approach, the protein is conjugated via at least one nucleophilic functional group added to the polymer. These nucleophilic functional groups include but are not limited to: amine or hydrazide. For the above protein, the preferable reaction conditions are at 4° C. and in slightly acidic pH to reduce the deamidation side reaction, which is known to occur at alkaline pH (greater than 7) at asparagine and glutamine residues. The amount of intact activated polymer employed is generally 1- to 10-fold excess of the activated polymer over the caroboxylated activated protein. Generally, the reaction process involves reacting the activated polymer with the protein in a 2 to 1 (polymer to protein) ratio. Typically, the reaction is carried out in a MES buffer pH 4.5, at 4° C. for from about 1 hour to about 8 hours. Following the conjugation, the desired conjugated protein is recovered and purified by liquid chromatography or the like.

The reaction conditions for effecting conjugation further include conducting the above attachment reactions at pH about 3-6, more preferably at pH 4-5, if the reactive group of the protein is a free histidine group. Using the above approach, the protein is conjugated via at least one terminal imidazole-reactive group added to the polymer. These imidazole-reactive groups include but are not limited to: N-hydroxysuccinimide (NHS) esters and anhydride. The amount of intact activated polymer employed is generally 1- to 10-fold excess of the activated polymer over the protein which is in either monomeric or multimeric. Generally the reaction process involves reacting the activated polymer with the protein in a 2 to 1 (polymer to protein) ratio. Typically the reaction is carried out in an acetate buffer, pH 4-5, 100 mM NaCl, at 4° C. for from about 2 hours to about 6 hours. Following the conjugation, the desired conjugated protein is recovered and purified by liquid chromatography or the like.

Successful conjugation of water-soluble polymers to therapeutic polypeptides has been previously described in U.S. Pat. No. 4,487,325, U.S. Pat. No. 5,824,784 and U.S. Pat. No. 5,951,974, each of which is incorporated herein in its entirety by reference.

In a further aspect, the present invention provides for pharmaceutical compositions comprising a therapeutically effective amount of the composition of the instant invention, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Composition of the instant invention may be employed alone or in conjunction with other compounds, such as therapeutic compounds.

The pharmaceutical composition will be adapted to the route of administration, for instance, by a systemic or an oral route. Forms of systemic administration include injection, typically by intravenous injection. Other injection routes, such as subcutaneous, intramuscular, or intraperitoneal, can be used. Alternative means for systemic administration include transmucosal and transdermal administration using penetrants, such as bile salts or fusidic acids or other detergents. In addition, if a composition of the instant invention can be formulated in an enteric or an encapsulated formulation, oral administration may also be possible. Administration of these compositions may also be topical and/or localized, in the form of salves, pastes, gels, and the like. Other routes of administration could include pulmonary or nasal delivery, either using solution or dry power formulation.

The dosage range required depends on the precise composition of the instant invention, the route of administration, the nature of the formulation, the nature of the subject's condition, and the judgment of the attending practitioner. Suitable dosages, however, are in the range of 0.1-1000 μg/kg of subject. Wide variations in the needed dosage, however, are to be expected in view of the variety of compositions available and the differing efficiencies of various routes of administration. For example, oral administration would be expected to require higher dosages than administration by intravenous injection. Variations in these dosage levels can be adjusted using standard empirical routines for optimization, as is well understood in the art.

The present invention may be embodied in other specific forms, without departing from the spirit or essential attributes thereof, and, accordingly, reference should be made to the appended claims, rather than to the foregoing specification or following examples, as indicating the scope of the invention.

All publications including, but not limited to, patents and patent applications, cited in this specification or to which this patent application claims priority, are herein incorporated by reference as if each individual publication were specifically and individually indicated to be incorporated by reference herein as though fully set forth.

EXAMPLES

Example 1

Prediction of PEGylation Sites Based upon Human and Murine IL-18 Crystal Structures:

Pegylation of human IL-18 (SEQ ID NO: 1) at Cys38 and Cys68 (the two native, surface-exposed cysteines) produced molecules with low activity. Therefore, we endeavored to identify sites in human IL-18 for mutation to Cys with subsequent pegylation, without interfering with the desired biological activity.

The crystal structure of mouse IL-18 has been solved (U.S. application Ser. No. 10/640,524, filed Aug. 13, 2003). It is apparent that IL-18 and IL-1β are similar in their core structures while differing in their surface loops. The structure of human IL-18 is expected to be very similar to the murine IL-18 structure because of the high sequence homology (65% identical). Using the crystal structure of murine IL-18, surface and loop residues can be mapped onto human IL-18.

We aimed to pegylate a residue at the tip of a flexible surface loop of IL-18 that is not implicated in interactions with the IL-18 receptor. We assume that IL-18 will interact with its receptor in a way similar to the IL-1β:IL-1β receptor interaction. The mouse IL-18 coordinates were superimposed onto the coordinates of human IL-1β from the complex of human IL-1β with IL-1β receptor (Vigers, et al. in Nature 386:190, 1997; PDB code 1ITB) in a three-dimensional overlay. The coordinates of the complex of human IL-1β receptor with the IL-1β receptor antagonist (Schreuder, et al., in Nature 386:194, 1997; PDB code 1IRA) were also used in modeling the binding mode of IL-18 to its receptor. From these overlays, we selected Asn78, Glu121, Leu144, and the C-terminus as the least likely to interact with the receptor, and therefore, good sites for mutation to cysteine and subsequent attachment of polyethyleneglycol to make pegylated IL-18. The C-terminal amino acid (D157) and Leu144 of human IL-18 were separately mutated to Cys and then PEGylated. The two resulting modified IL-18 molecules exhibited activity.

Example 2

Substitution Mutation Designs:

Based on the murine IL-18 crystal structure (U.S. application Ser. No. 10/640,524, filed Aug. 13, 2003), and later confirmed by the native human IL-18 crystal structure (PCT Application WO 03/089,653, published Oct. 30, 2003), a pegylation strategy was devised whereby monoPEG is attached to free cysteines away from the predicted receptor binding regions in order to minimize negative effects on biological activity. Native human IL-18 contains four cysteines, C38, C68, C76, and C127, as underlined in the amino acid sequence of mature human IL-18 shown in FIG. 1 (SEQ ID NO:1). Two of these, C38 and C68, are accessible for pegylation as predicted by the crystal structure. Pegylated native human IL-18 is dual-pegylated at both C38 and C68 and exhibits reduced in vitro biological activity (Table 1). Monopegylation is achieved either by substituting one of the native cysteines with a non-reactive amino acid and pegylating at the remaining reactive cysteine, or by substituting both native cysteines and substituting a free cysteine elsewhere in the molecule.

A series of human IL-18 substitution mutants was generated by site-directed mutagenesis (T. A. Kunkel (1985), Proc. Natl. Acad. Sci. USA 82:488-492.). All of these were expressed in E. coli in the pro form with an N-terminal six histidine purification tag (FIG. 3) (SEQ ID NO:3). ProIL-18 was subsequently activated to the mature form in vitro using separately purified caspase-5. All IL-18 mutations express efficiently and were purified with equivalent yields using this method. Alternative methods for producing active IL-18 in vitro or intracellularly with caspases 1, 4, and 5, and ubiquitin-specific protease have been described in detail in PCT WO 01/098455, published on Dec. 27, 2001. These methods are all suitable to the production of any of the IL-18 mutant designs disclosed in this application.

The substitution mutation designs, along with the corresponding sites for monopegylation within these, and the in vitro activity of pegylated and non-pegylated forms are summarized below in Table 1. Monopegylation of native IL-18 was achieved at cysteine 38 or cysteine 68 (FIG. 1, first two underline) (SEQ ID NO:1). Monopegylation within the native IL-18 molecule leads to about a five-fold reduction in biological potency in KG-1 IFN secretion assays compared to non-pegylated native IL-18. On the other hand, monopegylation at the free native cysteine 68 is achieved by substitution of C38 with serine (FIG. 4, underlined) (SEQ ID NO:4). Monopegylation at cysteine 68 within this molecule leads to about a two-fold reduction in biological potency in KG-1 IFN secretion assays compared to non-pegylated native IL-18. In contrast, the activity of the non-pegylated form of this substitution was not significantly reduced from native IL-18 (Table 1A).

Additional substitution designs were made based on the crystal model of human IL-18 for pegylation on exposed loops of the -trefoil structure, away from predicted receptor binding interaction sites. Four sites, N78, E121, L144, and D157, were chosen for cysteine substitutions. There may be other suitable residues for substitution mutations along the hIL-18 protein, but these four residues were chosen first. In order to achieve monopegylation at these sites, free cysteine 38 was substituted with serine and cysteine 68 was substituted with either serine or aspartic acid. Serine was used because of its neutral properties and small size comparable to that of cysteine. Aspartic acid was chosen because of the presence of aspartic acid in IL-18 of other species in a location relative to cysteine in human. FIGS. 5-10 show the amino acid sequences (SEQ ID NOs: 5-10, respectively) of each of these rational designs. Each substitution mutation is underlined. It was observed a decrease in activity in the biological potency assay for all muteins following pegylation. Based on the relative activities of pegylated and monopegylated forms, two pegylation sites, L144 and D157, were chosen and tested in subsequent in vitro and in vivo assays. Furthermore, C68S substitution was chosen due to the neutral properties of this residue substitution over C68D. Therefore, mutation designs C38S, C68S, L144C, and C38S, C68S, D157C were used for monopegylation at C144 and C157, respectively (FIGS. 9 and 10) (Tables 1A and 1B) (SEQ ID NOs:9 and 10, respectively).

TABLE 1A

| Substitution | Pegylation site(s) | Potency*/ non-pegylated | Potency*/ pegylated - 20K |
|---|---|---|---|
| Native (SEQ ID NO: 1) | C38 and C68 | 5.3 | 46 |
| C38S (SEQ ID NO: 4) | C68 | 9.6 | 24 |
| C38S, C68D, N78C (SEQ ID NO: 5) | C78 | 183 | 18 |
| C38S, C68D, E121C (SEQ ID NO: 6) | C121 | 10 | 26 |

*in vitro potency ($EC_{50}$) detected in a KG-1 IFNγ secretion assay

TABLE 1B

| Substitution | Pegylation site(s) | Potency*/ non-pegylated | Potency*/ pegylated - 20K |
|---|---|---|---|
| C38S, C68D, L144C (SEQ ID NO: 7) | C144 | 20 | 492 |
| C38S, C68D, D157C (SEQ ID NO: 8) | C157 | 26 | 666 |
| C38S, C68S, L144C (SEQ ID NO: 9) | C144 | 40 | 632 |
| C38S, C68S, D157C (SEQ ID NO: 10) | C157 | 40 | 572 |

*in vitro potency ($EC_{50}$) detected in a KG-1 IFNγ secretion assay

Example 3

Purification Methods:

a. Purification of Cysteine Substitution Mutants of IL-18:

All of the mutants described above in Example 2 were expressed as a soluble proform in E. coli with an N-terminal hexahis tag for the detection of expression level and purification convenience. E. coli cells expressing hexahis/proIL-18 (SEQ ID NO:3) were suspended in a lysis buffer at 10 ml/g of cells. Lysis buffer contained 50 mM Tris HCl pH 8.0, 500 mM NaCl, 5% glycerol, 10 mM 2-mercaptoethanol (Buffer A), 1 µg/ml pepstatin A and 0.4 mM phenylmethylsulfonyl fluoride. Cells were homogenized in the lysis buffer and lysed by two passes through a microfluidizer (M110-Y, Microfluidics) at 12,000 psi. The cell lysate was centrifused at 30,000 g for 30 minutes to remove cell debris and the supernatant was applied to a NiNTA agarose column which was washed with three column volumes of Buffer A. The column was further washed with three column volumes of Buffer A containing 30 mM imidazole to remove nonspecific bound impurities and hexahis/proIL-18 was eluted with 300 mM imidazole in buffer A. The pool was dialyzed against 25 mM HEPES pH 7.5 containing 100 mM NaCl and 10 mM 2-mercaptoethanol (Buffer B). Buffer B was an optimum buffer for caspase reaction. The pool in Buffer B was added by caspase 5 at 1:100 w/w (caspase 5 vs. proIL-18) and incubated overnight at room temperature to complete the cleavage reaction. The reaction mixture was adjusted to 0.5 M NaCl, which was applied to NiNTA agarose column. Mature IL-18 flowed through the column, while hexahis/prodomain bound back to the column. Some E. coli proteins (impurities), which bound to and eluted from the first Ni NTA agarose column, also rebound to the column yielding much more pure mature IL-18. The unbound protein was adjusted to 25 mM DTT and incubated for one hour to restore all cysteines at reduced state, reducing BME adducts and disulfide bonds formed during purification. The reduced mature IL-18 solution was adjusted to pH 6.0 by adding 2 M phosphoric acid in order to avoid cysteine oxidation and concentrated with YM10 membrane. The concentrated sample was applied to Superdex 75 column equilibrated with 10 mM NaPhosphate pH 6.0 containing 0.15 M NaCl and 1 mM EDTA in order to exchange the buffer, to remove any aggregate, and to remove endotoxin suitable in in vivo studies. Mature IL-18 was eluted as a monomer from Superdex 75 column and molecular weight by LC/MS analysis was as expected from the calculated monomeric form from cDNA. DTNB titration showed that all four cysteines are the reduced form.

b. Purification of PEGylated IL-18:

The PEGylation reaction mixture containing PEGylated IL-18, free PEG, and unmodified IL-18, immediately after the reaction, was diluted with an equal volume of 2 M $(NH_4)_2SO_4$ in 25 mM MES pH 6.2 (Buffer C). The diluted reaction mixture was applied to Source 15 Phenyl (Pharmacia) column which was washed with 1.5 column volume of 1 M $(NH_4)_2SO_4$ in Buffer C. The column was eluted with a 5 column volume of linear gradient to 0.5 M $(NH_4)_2SO_4$ in Buffer C. Free IL-18 eluted the first followed by free PEG and PEGylated IL-18 eluted the last. Fractions containing PEGylated IL-18 were pooled and concentrated with YM10 membrane and applied to size exclusion column, Superdex 200 prep grade (Pharmacia), which was preequilibrated and eluted with Buffer B. Superdex 200 removed any remaining free IL-18, free PEG, any aggregates, and endotoxin. Fractions containing PEGylated IL-18 were pooled and concentrated to ~5-6 mg/ml.

Example 4

Preparation of PEGylated IL-18:

The general procedure of preparation of PEGylated IL-18 is described below. An appropriate amount of methoxy polyethylene glycol maleimide (MAL MPEG) with an average molecular weight of 20,000, 30,000 or 40,000 Daltons was added (either as a solid or predissolved in aqueous or organic solvent) to a 2.5 mg/mL solution of the IL-18 in a phosphate buffer pH 6.0 -6.5. MAL MPEG was added to the protein solution with an excess molar amount of MAL MPEG. The reaction was allowed to proceed at 5° C. for 1-12 hours. At the end of the reaction, excess amount (e.g., 20×) of cysteine (0.5 M) was added to quench the reaction. At this stage, the reaction mixture was found to consist mainly of mono-, di-, and non-PEGylated IL-18 when wild type human IL-18 was used for PEGylation. In the case of using human IL-18 substitution mutant (as discussed in the previous sections), the reaction mixture was found to consist mainly mono-PEGylated and non-PEGylated IL-18 proteins (see FIG. 11).

a. Physicochemical Characterization

Four analyses were performed to characterize each sample: (1) SDS-PAGE, (2) reverse-phase liquid chromatography (RP-HPLC), (3) molecular weight determination (LC/MS) and (4) peptide mapping.

b. Degree of PEGylation

The degree of PEGylation (i.e., the number of PEG molecules attached to a single protein) was analyzed by sodium dodecyl sulfate polyacrylamide gel electrophoresis or RP-HPLC. Samples of human IL-18 or murine IL-18 PEGylation reaction mixture were run under reduced conditions at a load of 10.0 µg per lane on 4-12% Bis-Tris polyacrylamide gradient precast gels. Proteins were detected and quantitated after staining with Coomassie R-250. Quantitation was done by laser densitometry.

The degree of PEGylation could also be analyzed using a RP-HPLC method. Samples of reaction mixture were run under 1 mL/min flow rate and gradient 8.6%/min of mobile phase B (mobile phase A: 0.1% trifluoroacetic acid in water, mobile phase B: 0.1% TFA in 80% acetonitrile/water) using a POROS R2/H column with column temperature at 40° C.

c. Site of PEGylation-Development of Tryptic Peptides Map Method

To verify the location of the attachment of the PEG to the exact location on the protein, purified PEGylated IL-18 samples were analyzed by peptide mapping. Tryptic mapping of IL-18 was adapted from of a previous method (J. Bongers, et al., *J. Pharm. Biomed Anal.*, 21: 1099-1128 (2000)) and employs a direct S-carboxymethylation of the cysteines (free sulfhydryls) in IL-18: Samples (2.5 mg) were evaporated to dryness under vacuum, dissolved in 0.5 mL of a freshly prepared 20 mM sodium iodoacetate in 6 M guanidine.HCl, 1.2 M Tris/HCl buffer (pH 8.4), placed at RT in the dark for 40 min, and then immediately buffer-exchanged into 50 mM Tris/HCl, 1 mM CaCl2 (pH 8.1) digestion buffer on Bio-Gel P-6DG gel columns (BioRad Econ-Pac 10DG). Proteolytic digestions with trypsin (TPCK-treated Worthington), Lys-C (Wako), and Glu-C (Worthington) were all at 100/1 wt:wt S/E for 2 mg/mL CM-Cys IL-18 substrate at 37° C. for 2 hours. RP-HPLC mapping: Vydac 218MS52 C18 column (2.1×250 mm); 55° C.; 0 to 32% CH3CN(0.05% TFA) in 60 min; 0.2 mL/min, detection at 215/280 nm w/diode-array and Agilent G1946A MS detector (MSD) w/source. Smaller samples (50-300 μg) were run by a semi-micro version of the above procedure employing Bio-Rad Micro Bio-Spin Bio-Gel P-6DG gel columns.

Current peptide mapping methods typically employ DTT reduction of cysteine disulfide bridges followed by S-carboxymethylation of the resulting cysteines (reduction/alkylation). This unfolding (denaturing) step is often needed for successful proteolysis ("digestion"). However, in contrast to the oxidized "half-cysteines" (bridged) in most proteins, the 4 cysteine residues in hIL-18 are already reduced. Therefore, we have implemented a direct S-carboxymethylation in our peptide mapping method for IL-18 to replace the more usual reduction/alkylation procedure. Quantitative yields of fully S-carboxymethylated IL-18 (4×CM-Cys) were found by electrospray ionization LC/MS (MW 18449 Da theor, 18453 Da found). This is good evidence of the validity of the direct alkylation and confirms the existence of 4 mole equivalents of intact cysteine thiols. The advantage of direct alkylation is that it preserves information about the "chemical integrity" of the cysteines in IL-18 that would be lost by the usual reduction/alkylation procedure. For example, this peptide mapping procedure with direct carboxymethylation of the cysteines allows one to detect, not only PEGylation at cysteine residue, but also small amounts of air-oxidation of cysteines to form cysteine disulfides.

Figure 12:
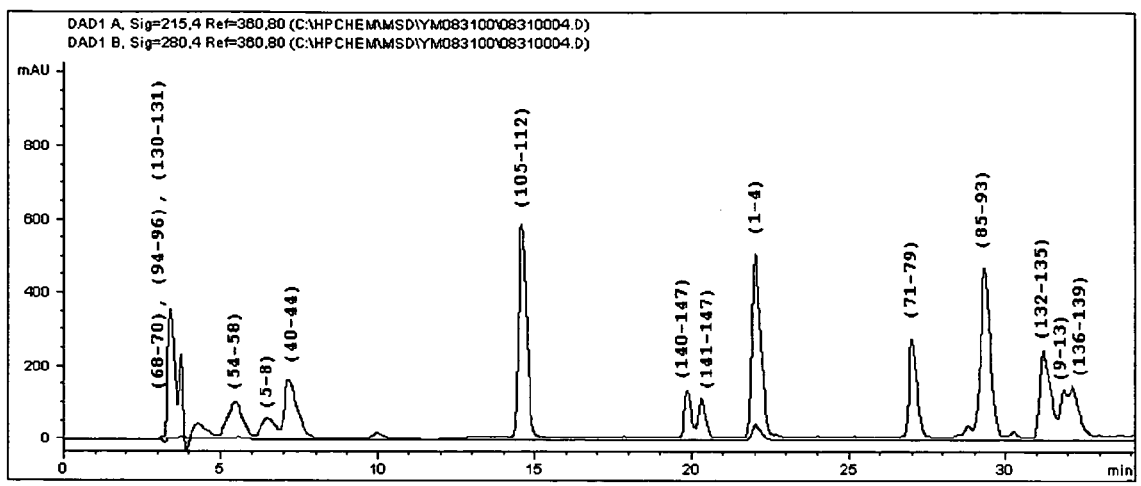
FIG. 12 shows a RP-HPLC tryptic map for wild type human IL-18 showing labeled peaks for peptides listed in Table 2. Peptides were identified by electrospray-ionization LC/MS. Detection at 215 and 280 nm.
Figure 12:
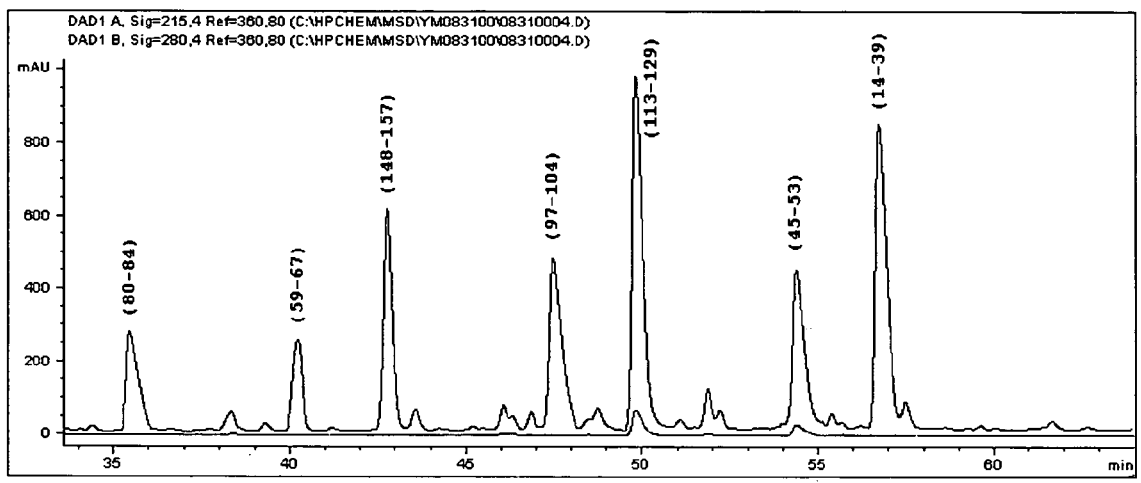

As a result of trypsin digestion, twenty predicted peptide fragments could be generated (see Table 2 below), and the individual peptide fragment can be separated and identified by RP-HPLC and LC/MS (FIG. 12). The peptide map approach is being used to identify the site of PEGylation, i.e., to which amino acid residue(s) were the polyethylene glycol molecules attached. FIG. 12 shows "mirror plot" comparison of the tryptic maps of monoPEG(20K) human wild type IL-8 versus an unmodified human wild type IL-18 control. The four cysteine-containing tryptic peptides, (14-39), (68-70), (71-79), and (113-129) corresponding to cysteines 38, 68, 76, and 127, respectively, are labeled for the control. The large decrease in peak area versus control for the (14-39) peak in the tryptic map of monoPEG human IL-18 indicates extensive PEGylation at cysteine 38 (ca. 90%). The late-eluting peak labeled "PEG-Cys38 (14-39)" was isolated and found to contain 90% PEG-Cys38 (14-39) and 10% PEG-Cys68 (68-70) by N-terminal sequencing (FIG. 12). Detection took place at 215 nm. This results showed that the mono-PEGylated human IL-18 was PEGylated predominately via the cysteine 38 position. This result is surprising and unexpected, due to the fact that there are three other free cysteines available in the protein.

TABLE 2

Tryptic peptides predicted and found by LC-MS for S-carboxymethylated wild type IL-18. The four cysteine-containing peptides are indicated in boldface.

| # | Peptide | $t_{ret}^a$ (min) | MW theor (Da) | MW found[b] (Da) | Sequence and Corresponding Sequence Identifier Number, if required |
|---|---|---|---|---|---|
| 1 | (1-4) | 22.0 | 513.3 | 513.2 | YFGK (SEQ ID NO: 11) |
| 2 | (5-8) | 6.5 | 475.3 | 475.3 | LESK (SEQ ID NO: 12) |
| 3 | (9-13) | 31.8 | 586.4 | 586.5 | LSVIR (SEQ ID NO: 13) |
| 4 | (14-39) | 56.8 | 3113.4 | 3113.4 | NLNDQVLFIDQGNRPLFEDMTDSDCR (SEQ ID NO: 14) |
| 5 | (40-44) | 7.1 | 571.3 | 571.3 | DNAPR (SEQ ID NO: 15) |
| 6 | (45-53) | 54.4 | 1114.6 | 1114.7 | TIFIISMYK (SEQ ID NO: 16) |
| 7 | (54-58) | 5.4 | 601.3 | 601.3 | DSQPR (SEQ ID NO: 17) |
| 8 | (59-67) | 40.2 | 904.5 | 904.5 | GMAVTISVK (SEQ ID NO: 18) |
| 9 | (68-70) | 3.4 | 436.2 | 436.1 | CEK |
| 10 | (71-79) | 27.0 | 1051.5 | 1051.5 | ISTLSCENK (SEQ ID NO: 19) |
| 11 | (80-84) | 35.5 | 606.4 | 606.4 | IISFK (SEQ ID NO: 20) |
| 12 | (85-93) | 29.3 | 1056.5 | 1056.5 | EMNPPDNIK (SEQ ID NO: 21) |
| 13 | (94-96) | 3.4 | 362.2 | 362.2 | DTK |
| 14 | (97-104) | 47.5 | 1024.5 | 1024.5 | SDIIFFQR (SEQ ID NO: 22) |
| 15 | (105-112) | 14.6 | 852.4 | 852.4 | SVPGHDNK (SEQ ID NO: 23) |
| 16 | (113-129) | 49.9 | 2076.8 | 2076.8 | MQFESSSYEGYFLACEK (SEQ ID NO: 24) |
| 17 | (130-131) | 3.4 | 303.2 | 303.3 | ER |
| 18 | (132-135) | 31.2 | 521.3 | 521.3 | DLFK (SEQ ID NO: 25) |
| 19 | (136-139) | 32.1 | 485.4 | 485.4 | LILK (SEQ ID NO: 26) |

TABLE 2-continued

Tryptic peptides predicted and found by LC-MS for S-carboxymethylated wild type IL-18. The four cysteine-containing peptides are indicated in boldface.

| # | Peptide | $t_{ret}$[a] (min) | MW theor (Da) | MW found[b] (Da) | Sequence and Corresponding Sequence Identifier Number, if required |
|---|---------|---------|---------|---------|---------|
| 20 | (140-140) | nf | 146.1 | nf | K |
| 21 | (141-147) | 20.3[c] | 832.4 | 832.5 | EDELGDR (SEQ ID NO: 27) |
| 22 | (148-157) | 42.8 | 1182.5 | 1182.5 | SIMFTVQNED (SEQ ID NO: 28) |

[a]Retention times ($t_{ret}$) refer to RP-HPLC tryptic map in FIG. 12.
[b]Molecular weights (MW) determined by electrospray ionization LC/MS tryptic mapping.
[c]Also found roughly equal amount of 140-147 peptide (KEDELGDR) (SEQ ID NO: 29) from "incomplete cleavage" eluting at 19.8 min.

d. Tryptic Mapping of Purified MonoPEGylated Wild Type Human IL-18

Figure 14:
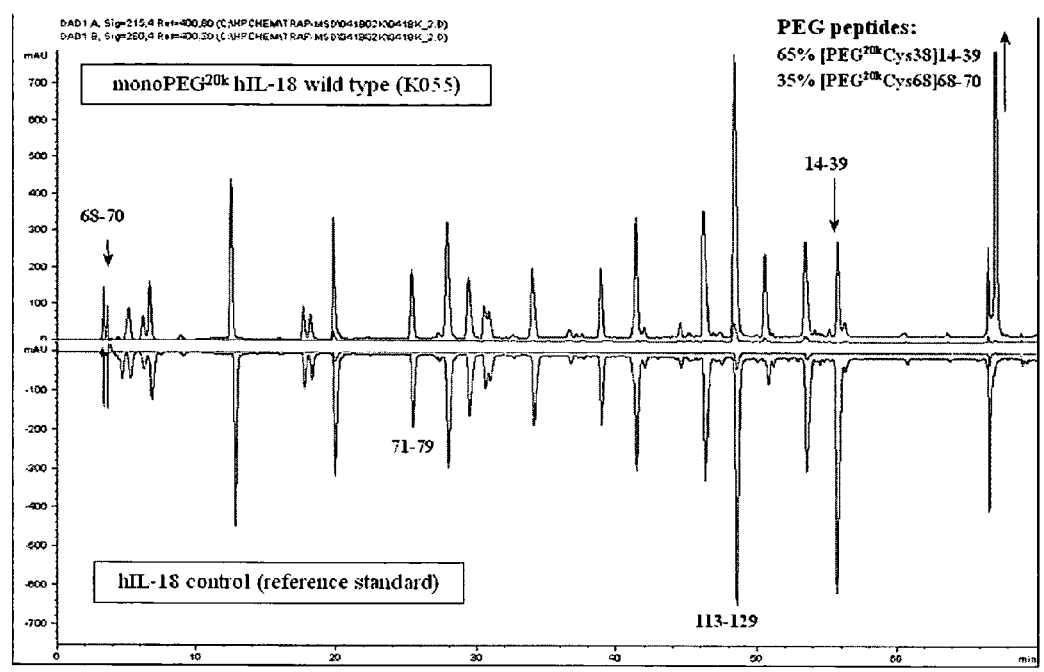
FIG. 14 shows tryptic mapping of wild type human IL-18 (SEQ ID NO: 1) and purified monoPEGylated (20K) product.

The tryptic map data in FIG. 14 for the purified monoPEGylated wild type hIL-18 product shows PEGylation exclusively at the solvent-accessible cysteines 38 and 68, to the approximate extents of 65 and 35±5 mole%, respectively, based on the decrease in relative peak area versus control for the 14-39 peptide peak eluting at 56 min. No detectable PEGylation occurred at the buried cysteines, 76 and 127, as evidenced by the quantitative recoveries of the 71-79 and 113-129 tryptic peptides in the map. These results are based on the observed decreases, or lack thereof, in the relative peak areas for the cysteine-containing tryptic peptides in the monoPEGylated hIL-18 map versus the nonPEGylated hIL-18 control map with the concurrent appearance of a late-eluting hydrophobic peak containing the PEGylated peptides pool. The approximate 65 to 35 mole% distribution of PEG on cysteines 38 and 68 was further confirmed by extracted-ion current traces from the LC/MS/MS-MS data.

e. N-terminal Sequencing of PEGylated Tryptic Peptides from Purified MonPEGylated Human IL-18 C38S,C68D, L144C (SEQ ID NO:7) and C38S,C68D,D157C (SEQ ID NO:8) Muteins In addition to determining the sites and extents of PEGylation by differences versus control in peak areas for the nonPEGylated peptides in RP-HPLC tryptic map chromatograms, we also made direct analysis of the PEGylated peptide fragments released from protein. Such direct information on the PEGylated peptides would be related by "mass balance" to the complementary indirect evidence from differences in peak areas for the nonPEGylated peptides. As mentioned earlier, these different PEGylated peptides all co-elute in the RP-HPLC tryptic map as a single late-eluting peak containing the entire unresolved pool of PEGylated peptide species. Because the PEGylated peptides are not amenable to on-line electrospray mass spectrometry with ion-trap or quadrupole mass analyzers, we employed a micro-chemical Edman N-terminal sequencing to analyze the pool of PEGylated peptides collected from the RP-HPLC tryptic map.

Edman N-terminal sequencing data for the isolated RP-HPLC late-eluting peaks (PEGylated peptide pool) for the monoPEG20k hIL-18 C38S,C68D,L144C (SEQ ID NO:7) indicated 98.3 mole% PEG at the surface-loop cysteine 144 and 1.3 mole% PEG at the partially-buried cysteine 127. Edman sequencing for the monoPEG20k hIL-18 C38S, C68D,D157C (SEQ ID NO:8) PEGylated tryptic peptide pool yielded >99.5 mole% PEG at the C-terminal solvent-exposed cysteine 157 and no detectable PEG at the partially-buried cysteine 127 nor any other additional site.

Figure 13:
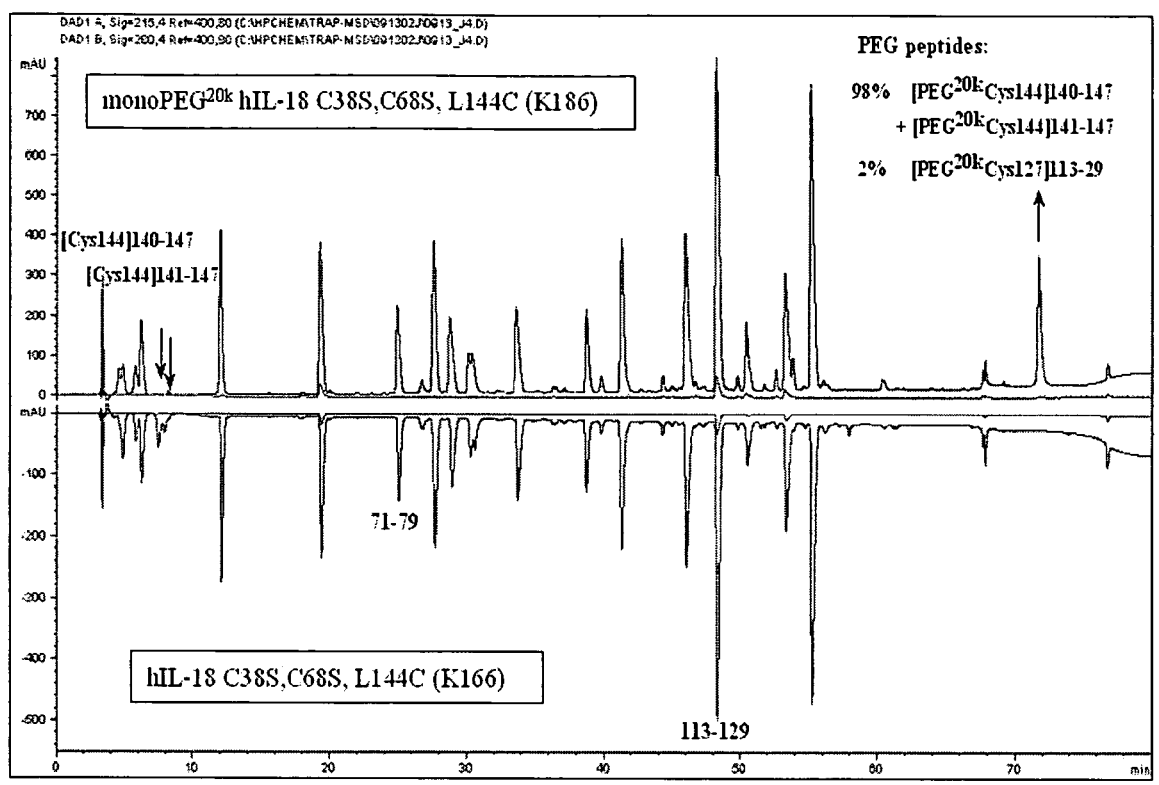
FIG. 13 shows tryptic mapping of human IL-18 substitution mutant C38S,C68S,L144C (SEQ ID NO: 9).
Figure 15:
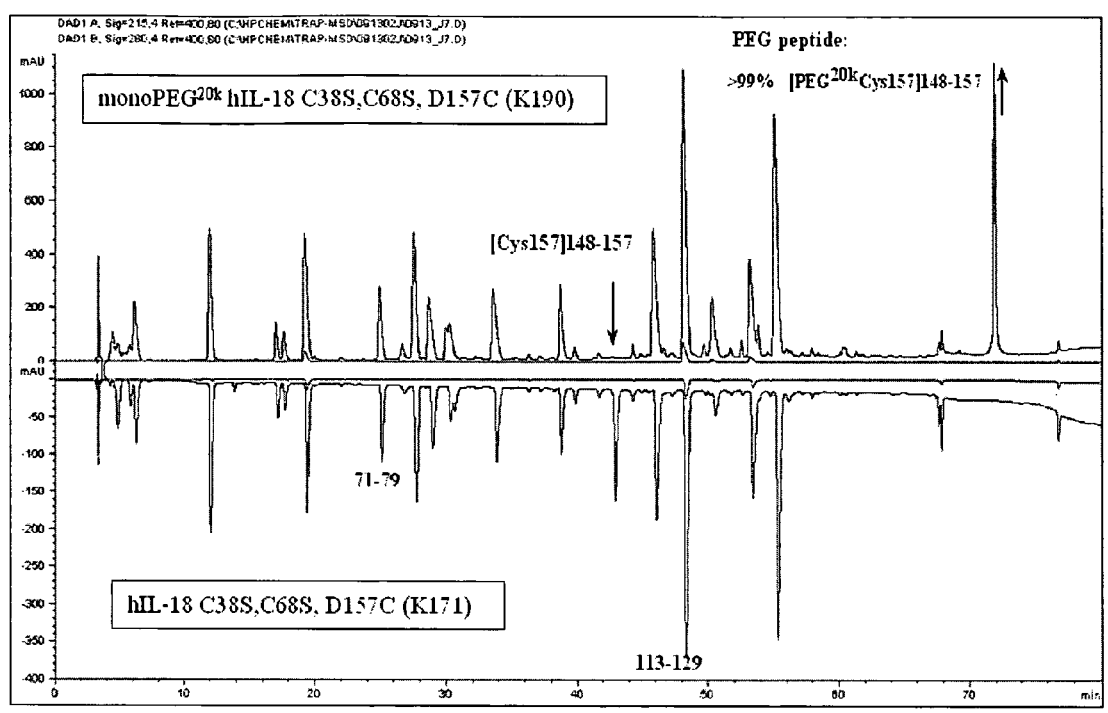
FIG. 15 shows tryptic mapping of monoPEG$^{20k}$ human IL-18 substitution mutant C38S,C68S,D157C (SEQ ID NO: 10).

Thus, for monoPEG20k hIL-18 C38S,C68D,L144C (SEQ ID NO:7), the sequencing data reveal approximately 1-2% of competing PEGylation at the partially-buried cysteine 127 in addition to the desired PEGylation at cysteine 144. No such competing PEGylation at cysteine 127, nor any other site, was detectable for monoPEG20k hIL-18 C38S, C68D,D157C (SEQ ID NO:8), on the other hand. These sequencing data are consistent with a slightly more nucleophilic (reactive) cysteine at residue 157 as opposed to residue 144. The slightly more favorable reactivity towards PEGylation for the C-terminal cysteine 157 in the folded protein versus that for the internal loop cyteine 144 may perhaps reflect some combination of a slightly higher degree of solvent-accessibility for this residue, and/or thermal mobility, different local electrostatic environment, and higher acidity of the thiol.

f. Tryptic Mapping of Human IL-18 Substitution Mutant (C38S,C68S,L144C (SEQ ID NO:9) and C38S,C68S, D157C (SEQ ID NO:10) Substitution Mutants) and Purified Mono-PEGylated Substitution Mutants Tryptic mapping data (FIGS. 13 and 15) confirm the expected chemical structures for human IL-18 substitution mutants C38S,C68S,L144C (SEQ ID NO:9) and C38S, C68S,D157C (SEQ ID NO:10) and the respective purified monoPEGylated conjugates. The RP-HPLC data are consistent with >95% site-specific quantitative PEGylation at the engineered surface cysteines at residues 144 and 157, respectively. And, for both substitution mutants, the carboxymethylated tryptic peptides containing the buried cysteines at residues 76 and 127 were recovered in nearly quantitative yields versus a control tryptic map of wild type human IL-18 reference standard, and virtually no other significant chemical modifications (side reactions) were observed in the final products.

Example 5

Affinity Measurements (Kinetic Analysis of IL-18 Binding to IL-18Rα chain and IL-18BP)

The biological effects of human IL-18 are related to binding to its cell surface receptor and, possibly, by its binding to the natural antagonist, IL-18 BP. Binding assays for IL-18 and either the alpha chain of the receptor, or IL-18 BP, were developed using the BIAcore® instrument, a surface plasmon resonance-based biosensor. This technology involves immobilizing one bio-molecule on a sensor chip and monitoring its interaction with a second component in solution in real time.

The IL-18 substitution mutants had reduced affinities for the receptor (6-16-fold). However, binding affinity to IL-18 BP was not affected. In contrast, pegylation significantly reduced affinities for both receptor (13-114-fold) and IL-18 BP (10-176-fold) (Table 3).

TABLE 3

Summary of affinities (M) of IL-18 in binding to IL-18 Rα and IL-18 BP

| IL-18s | IL-18 Rα | IL-18 BP |
|---|---|---|
| IL-18 wild-type (SEQ ID NO: 1) | 3.2 (±0.1) × $10^{-8}$ | 1.35 (±0.06) × $10^{-10}$ |
| IL-18 C144 (C38S, C68D, L144C) (SEQ ID NO7) | 2.22 (±0.07) × $10^{-7}$ | 1.01 (±0.12) × $10^{-10}$ |
| IL-18 C144PEG20K | 2.69 (±0.07) × $10^{-6}$ | 1.16 (±0.03) × $10^{-9}$ |
| IL-18 C144PEG30K | 4.26 (±0.03) × $10^{-6}$ | 1.51 (±0.05) × $10^{-9}$ |
| IL-18 C144PEG40K | 5.35 (±0.09) × $10^{-6}$ | 4.71 (±0.09) × $10^{-9}$ |
| IL-18 C157 (C38S, C68D, D157C) (SEQ ID NO: 8) | 1.96 (±0.12) × $10^{-7}$ | 1.34 (±0.08) × $10^{-10}$ |
| IL-18 C157PEG20K | 5.16 (±0.03) × $10^{-6}$ | 5.53 (±0.21) × $10^{-9}$ |
| IL-18 C157PEG30K | 5.33 (±0.15) × $10^{-6}$ | 4.91 (±0.45) × $10^{-9}$ |
| IL-18 C157PEG40K | 2.29 (±0.1) × $10^{-5}$ | 2.36 (±0.2) × $10^{-8}$ |
| IL-18 C144 (C38S, C68S, L144C) (SEQ ID NO: 9) | 5.34 (±0.11) × $10^{-7}$ | 1.56 (±0.16) × $10^{-10}$ |
| IL-18 C144PEG20K | 5.19 (±0.13) × $10^{-6}$ | 1.56 (±0.08) × $10^{-9}$ |
| IL-18 C144PEG30K | 8.26 (±0.16) × $10^{-6}$ | 1.51 (±0.04) × $10^{-9}$ |
| IL-18 C157 (C38S, C68S, D157C) (SEQ ID NO: 10) | 4.1 (±0.11) × $10^{-7}$ | 1.63 (±0.04) × $10^{-10}$ |
| IL-18 C157PEG20K | 5.5 (±0.4) × $10^{-6}$ | 1.27 (±0.05) × $10^{-9}$ |
| IL-18 C157PEG30K | 6.34 (±0.16) × $10^{-6}$ | 1.29 (±0.06) × $10^{-9}$ |

Example 6

NF-κB Signaling

The effect of IL-18 is mediated by binding to a heterodimeric surface receptor composed of α- and β-chains. While the α-chain alone can bind IL-18, both sub-units are required to form the functional high affinity IL-18 receptor that can activate intracellular signaling pathways and mediate the biological effects of IL-18 on target cells. The transcription factor NF-κB is a key mediator of the immunomodulatory effects of IL-18. IL-18 receptor signaling induces the activation of IKK protein kinases, which, in turn, phosphorylate the NF-κB inhibitor IκBα. The phosphorylated IκBα is degraded, allowing release of free NF-κB which translocates to the nucleus and activates gene transcription. Multiple IL-18 muteins were evaluated in this assay. From these studies, the IL-18 muteins containing C38S, C68D, L144C (SEQ ID NO:7), C38S, C68S L144C (SEQ ID NO:9), C38S, C68D, D157C (SEQ ID NO:8), and C38S, C68S, D157C (SEQ ID NO:10) were identified as the most potent.

The data in Table 4 summarize the results from the NF-κB bioassay with several different molecules. Relative to the native IL-18 (SEQ ID NO:1), the IL-18 substitution mutants, C38S, C68D, L144C (SEQ ID NO:7) and C38S, C68D, D157C (SEQ ID NO:8) had roughly a 10-fold reduction in potency. Further decreases in potency were seen with the pegylated molecules. In general, the 20K and 30K PEG muteins were more potent than the 40K PEG versions.

TABLE 4

Induction of NF-κB activity by IL-18, IL-18 muteins and their pegylated derivatives

| IL-18 | Pegylation | NF-κB KG-1 EC50 (ng/ml) | av. |
|---|---|---|---|
| HIL-18 (SEQ ID NO: 1) (KG-1 assay) | None | 0.06, 0.07, 0.08, 0.21, 0.32, 0.4, 0.8 | 0.3 |
| C38S, C68D, L144C | None | 1.6, 3.5 | 2.6 |
| (SEQ ID NO: 7) | 144C-20K | 58, 66, 42 | 55.3 |
| | 144C-30K | 38 | 38 |
| | 144C-40K | 271, 330 | 300.5 |
| C38S, C68S, L144C | None | 1.1, 4.3, 2.5 | 2.6 |
| (SEQ ID NO: 7) | 144C-20K | 71, 92 | 81.5 |
| | 144C-30K | 44 | 44 |
| C38S, C68D, D157C | None | 4.0 | 4.0 |
| (SEQ ID NO: 8) | 157C-20K | 30, 65, 17 | 37.3 |
| | 157C-30K | 94, 43 | 68.5 |
| | 157C-40K | 144, 61, 628 | 277.7 |
| C38S, C68S, D157C | None | 0.8, 3.2 | 2 |
| (SEQ ID NO: 8) | 157C-20K | 49, 59 | 54 |
| | 157C-30K | 47 | 47 |

*EC50 values determined in murine IL-18R-KG-1 cell line.

Example 7

Murine Pharmacodynamics (PD) Data for Human PEG IL-18 (IFNγ Induction)

Treatment of BALB/c mice with a single injection of murine IL-18 increased cytokine production. The most robust increases were found with IFNγ and GM-CSF. Because the IFNγ response was very rapid and extensive, this biomarker was used to compare the potency of pegylated IL-18 to the native IL-18 molecule. Human IL-18 (SEQ ID NO:1) and pegylated human IL-18 (SEQ ID NO:1) were administered at 10 or 100 μg doses by SC injection. Sera were collected at 2, 4, 6, 8, 12 and 16 hours post treatment and analyzed for IFNγ production. An equimolar dose of pegylated IL-18 induced higher circulating levels of IFNγ than non-pegylated IL-18. Peak levels of IFNγ for pegylated IL-18 were found between 4-16 hours, while non-pegylated IL-18 caused a peak between 2-4 hours. In spite of reduced affinity for the IL-18 α chain receptor (as shown in Table 3), or reduced activity in NF-kB cell-based assay (as shown in Table 4), pegylated human IL-18 (SEQ ID NO:1) showed an increase in IFNγ, an important PD marker for IL-18 molecules (Table 5).

TABLE 5

Induction of murine IFNγ by pegylated and non-pegylated human IL-18

| | IFN-γ pg/ml average | | | | | |
|---|---|---|---|---|---|---|
| | 2 hrs | 4 hrs | 6 hrs | 8 hrs | 12 hrs | 16 hrs |
| PEG-IL-18 | 37 | 595 | 830 | 1150 | 489 | 59 |
| IL-18 | 374 | 342 | 187 | 0 | | |

Example 8

NK Cytotoxicity of Pegylated and Non-pegylated IL-18 (SEQ ID NO:1) (ex vivo Murine System)

IL-18 is a Th1-dominant cytokine that activates NK cells. In this study, we aimed to measure NK cytotoxicity in response to human pegylated and non-pegylated IL-18 (SEQ ID NO:1). This assay is a direct measure of anti-tumor activity.

NK cell activity was measured by europium-release assays using murine YAC-1 cells (NK-sensitive T-cell lymphoma) as targets and BALB/c spleen cells from treated animals as effectors. Mice were given a single injection of human pegylated and non-pegylated IL-18 (equimolar) concentrations. Mice were sacrificed 18-24-hours post treatment. The splenocytes from treated animals (and controls) were combined with Europium labeled YAC-1 target cells and measured for europium release.

Pegylated IL-18 induced NK cytotoxicity in mice (Table 6). All human pegylated IL-18 forms showed ability to induce NK cytotoxicity (data not shown). The 20K pegylated IL-18 showed better activity than non-pegylated IL-18 at all effector: target ratios examined (Table 6). Again, in spite of reduced affinity for the IL-18-α chain receptor (as shown in Table 3) or reduced activity in NF-kB cell-based assay (as shown in Table 4), pegylation neither reduced, nor eliminated IL-18 dependent in vivo NK activation.

TABLE 6

NK cytotoxicity in mice

| Samples | Effector:Target ratios* | | | |
|---|---|---|---|---|
| | 200:1 | 100:1 | 50:1 | 25:1 |
| Non-pegylated IL-18 | 46 | 41 | 24 | 13 |
| Pegylated IL-18 | 66 | 62 | 53 | 37 |
| Vehicle | 6 | 7 | 7 | 5 |

*Numbers expressed as percent specific lysis

Example 9

Complex Formation with IL-18 Binding Protein

An immunoassay for the detection of complex between IL-18 (SEQ ID NO:1) and IL-18 binding protein (IL-18BP) was developed by using the IGEN® system. This assay uses a non-neutralizing mAb to human IL-18 (16D10 mAb, a ruthenium conjugated) and a non-blocking mAb to human IL-18BP (mAb 36, biotinylated). Human IL-18BP at 125 ng/ml was combined with 125 ng/ml of non-pegylated IL-18 or pegylated IL-18.

Pegylated IL-18 molecules had a reduced capacity to complex with IL-18BP (Table 7), which is in contrast to non-pegylated IL-18 which formed a complex.

TABLE 7

Complex formation with IL-18BP

| Pegylated/non-pegylated IL-18 molecules | ECL units |
|---|---|
| IL-18 | 1101269 |
| C144 non-PEG | 561129 |
| C144 20K PEG | 153831 |
| C157 non-PEG | 376830 |
| C157 20K PEG | 63476 |
| C38S single mutant | 746054 |
| C68 20K PEG | 49104 |

Example 10

Monkey Pharmacodynamics (PD) and Pharmacokinetics (PK) Data for PEG IL-18 and Substitution Mutants Thereof:

In response to pegylated IL-18 and non-pegylated IL-18, PD markers were assessed in Cynomolgus monkeys. Cynomolgus monkeys (3 males/group) received a single intravenous injection of 1 mg/kg of either non-pegylated IL-18 or pegylated IL-18. Blood samples were collected prior to dosing and at multiple time points over a 10-day period after dosing. Plasma was analyzed for drug and neopterin concentrations; leukocytes were then analyzed by flow cytometry for expression of the CD64 marker.

a: Monkey Pharmacodynamics (PD)

Cynomolgus monkey leukocytes were evaluated for changes in CD64 mean fluorescence intensity (MFI). Pegylated IL-18 and non-pegylated IL-18 increased CD64 expression between 1 and 3 days after dosing. Elevated CD64 expression on total leukocytes peaked on Day 3 and persisted until Day 10. The leukocyte CD64 MFI was higher (up to 2-fold) in response to pegylated IL-18 compared to non-pegylated IL-18 at every time point after dosing (Table 8). In total leukocytes, the CD64 MFI was statistically significantly higher for pegylated IL-18 than for non-pegylated IL-18.

Pegylated IL-18 and non-pegylated IL-18-induced neopterin production between 1 and 4 days after dosing, with the peak response at 24 or 48 hours. Fold induction and group mean concentrations of neopterin were generally higher in response to pegylated IL-18 (15-21 μg/ml on Day 2) than in response to non-pegylated IL-18 (13 μg/ml on Day 2) (Table 9). However, the differences did not reach statistical significance.

The CD64 marker on leukocytes significantly increased in expression in response to pegylated IL-18 compared to non-pegylated IL-18. This marker is expressed on cells of myeloid lineage, monocyte, macrophage, dendritic cells (DCs), and neutrophils. These cells play a role in the IL-18-induced immune response, and therefore are a relevant measure of pegylated IL-18 activity. The induction of neopterin was not statistically significant, but the increase in expression supports the in vivo advantage of pegylated IL-18 over non-pegylated IL-18.

TABLE 8

CD64 mean fluorescence intensity (MFI) on leukocytes from cynomolgus monkeys treated with 1 mg/kg pegylated or non-pegylated IL-18

| | | Monkey ID | | | | CD64 MFI on Leukocytes Time (hours) | |
|---|---|---|---|---|---|---|---|
| | Candidate | Day 0 (Pre-dose) | Day 1 (24) | Day 2 (48) | Day 3 (72) | Day 7 (168) | Day 10 (240) |
| IL-18 Pegylated | 2001 | 80.8 | 164.2 | 163.7 | 285.7 | 170.4 | 151.6 |
| | 2002 | 84.8 | 216.7 | 220.2 | 366.6 | 229.6 | 175.4 |
| | 2003 | 56.7 | 98.9 | 117.9 | 159.6 | 116.7 | 88.5 |
| | Mean ± SEM | 74.1 ± 8.8 | 159.9 ± 34.1 | 167.3 ± 29.6 | 270.6 ± 60.2 | 172.2 ± 32.6 | 138.5 ± 25.9 |
| IL-18 Non-pegylated | 3001 | 57.6 | 91.4 | 101.4 | 136.9 | 87.6 | 91.7 |
| | 3002 | 56.2 | 87.1 | 98.2 | 107.8 | 76.7 | 71.1 |
| | 3003 | 58.6 | 86.6 | 92.4 | 145.8 | 102.1 | 93.1 |
| | Mean ± SEM | 57.5 ± 0.7 | 88.4 ± 1.5 | 97.3 ± 2.6 | 130.2 ± 11.5 | 88.8 ± 7.4 | 85.3 ± 7.1 |

TABLE 9

Neopterin production in cynomolgus monkeys treated with 1 mg/kg pegylated IL-18 or non-pegylated IL-18

| | | Monkey ID | | | | | | Neopterin Concentration (nmol/L) Time (hours) | | | |
|---|---|---|---|---|---|---|---|---|---|---|---|
| | Candidate | Day 1 (Pre-dose) | Day 0.3 (8) | Day 1 (24) | Day 2 (48) | Day 3 (72) | Day 4 (96) | Day 7 (168) | Day 9 (216) | Day 11 (264) | Day 14 (336) |
| IL-18 Pegylated | 2001 | 6.9 | 10.1 | 21.7 | 18.3 | 14.6 | 12.7 | 10.0 | 9.0 | 9.1 | 7.5 |
| | 2002 | 3.8 | 4.7 | 13.2 | 13.7 | 9.9 | 7.9 | 5.0 | 4.9 | 4.3 | 3.9 |
| | 2003 | 7.4 | 7.3 | 17.1 | 12.1 | 9.2 | 9.3 | 7.8 | 7.1 | 7.7 | 5.8 |
| | Mean ± SEM | 6.0 ± 1.1 | 7.4 ± 1.6 | 17.4 ± 2.5 | 14.7 ± 1.8 | 11.3 ± 1.7 | 10.0 ± 1.4 | 7.6 ± 1.4 | 7.0 ± 1.2 | 7.0 ± 1.4 | 5.7 ± 1.0 |
| IL-18 Non-pegylated | 3001 | 8.3 | 10.6 | 18.4 | 15.7 | 12.8 | 10.9 | 8.1 | 7.5 | 7.0 | 8.4 |
| | 3002 | 7.4 | 9.1 | 15.9 | 15.9 | 13.5 | 12.2 | 12.0 | 11.1 | 11.6 | 11.1 |
| | 3003 | 4.6 | 6.1 | 9.3 | 10.3 | 8.3 | 6.8 | 5.9 | 4.6 | 4.7 | 4.3 |
| | Mean ± SEM | 6.0 ± 1.1 | 7.6 ± 1.3 | 12.6 ± 2.7 | 13.1 ± 1.9 | 10.9 ± 1.6 | 9.5 ± 1.6 | 9.0 ± 1.8 | 7.8 ± 1.9 | 8.1 ± 2.0 | 7.7 ± 2.0 |

* Bold values indicate peak response.

b: Monkey Pharmacokinetics (PK)

The PK data for pegylated and non-pegylated human IL-18 in Cynomolgus monkey are summarized in Table 10. The area under curve (AUC) for pegylated IL-18 of the 0-8 hours period was ~7-fold greater that the AUC of non-pegylated IL-18 for the entire 336 hour time course. For pegylated IL-18, the apparent t1/2 of the 0-8 hour phase was ~0.5 hours, whereas the t1/2 of the non-pegylated IL-18 initial phase (~43% of the total AUS) was ~7 minutes. The Cmax value for the pegylated IL-18 was ~4-fold greater than Cmax value for the non-pegylated IL-18 and was consistent with the drug initially distributing into the plasma compartment.

TABLE 10

Monkey pharmacokinetics (PK)

| Compound | Cmax (ng/mL) | AUC-$l_{-1}$ (ng · hr/mL) | $T_{1/2}$-$l_1$ (min) | $AUC_{(0-inf)}$ (ng · hr/mL) | Term. $T_{1/2}$ (hr) |
|---|---|---|---|---|---|
| Pegylated IL-18 | 22193 ± 3119 | 18950 ± 3659 | 36 ± 3 | 111619 ± 7809* | 53 ± 14* |
| Non-pegylated IL-18 | 5752 ± 582 | 1209 ± 126 | 7 ± 1 | 2840 ± 224 | 31 ± 7 |

All publications including, but not limited to, patents and patent applications, cited in this specification, are herein incorporated by reference as if each individual publication were specifically and individually indicated to be incorporated by reference herein as though fully set forth.

The above description fully discloses the invention, including alternative embodiments thereof. Modifications and improvements of the embodiments specifically disclosed herein are within the scope of the following claims. Without further elaboration, one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. A human IL-18 substitution mutant, wherein said mutant comprises from three to five amino acid substitutions in the sequence of SEQ ID NO:1, said substitutions being at from three to five amino acid residues chosen from the group consisting of: the cysteine at residue 38, the cysteine at residue 68, the cysteine at residue 76, the asparagine at residue 78, the glutamic acid at residue 121, the cysteine at residue 127, the leucine at residue 144, and the aspartic acid at residue 157.

2. The human IL-18 substitution mutant as claimed in claim 1, wherein said mutant contains a serine in place of cysteine at residue 38, an aspartic acid in place of cysteine at residue 68, and a cysteine in place of asparagine at residue 78 (SEQ ID NO:5).

3. The human IL-18 substitution mutant as claimed in claim 1, wherein said mutant contains a serine in place of cysteine at residue 38, an aspartic acid in place of cysteine at residue 68, and a cysteine in place of glutamic acid at residue 121 (SEQ ID NO:6).

4. The human IL-18 substitution mutant as claimed in claim 2, wherein said mutant contains a serine in place of cysteine at residue 38, an aspartic acid in place of cysteine at residue 68, and a cysteine in place of leucine at residue 144 (SEQ ID NO:7).

5. A human IL-18 substitution mutant, wherein said mutant comprises the amino acid sequence of (SEQ ID NO:8).

6. A composition comprising a polypeptide conjugated to a water-soluble polymer, wherein the polypeptide is the human IL-18 substitution mutant selected from the group consisting of SEQ ID NO: 5, 6, 7, 8, 9, and 10.

7. The composition as recited in claim 6, wherein the polypeptide comprises SEQ ID NO: 8 and wherein the conjugation between the polypeptide and the polymer is covalent.

8. The composition as recited in claim 6, wherein the polypeptide comprises SEQ ID NO: 8 and wherein the water-soluble polymer is a member chosen from the group of: polyethylene glycol homopolymers, polyethylene glycol copolymers, polypropylene glycol homopolymers, poly(N- vinylpyrrolidone), poly(vinyl alcohol), poly(ethylene glycol-co-propylene glycol), poly(N-2-(hydroxyproply)methyacrylamide), poly(sialic acid), poly(N-acryloyl morpholine), and dextran.

9. The composition as claimed in claim 8, wherein the water-soluble polymer is unsubstituted.

10. The composition as claimed in claim 8, wherein the water-soluble polymer is substituted at one end with an alkyl group.

11. The composition as claimed in claim 8, wherein the water-soluble polymer is a polyethylene glycol homopolymer.

12. The composition as claimed in claim 11, wherein the polyethylene glycol homopolymer is monomethoxy-polyethylene glycol.

13. The composition as claimed in claim 12, wherein the monomethoxy-polyethylene glycol is chosen from the group of linear monomethoxy-polyethylene glycol and branched monomethoxy-polyethylene glycol.

14. The composition as claimed in claim 13, wherein the polyethylene glycol homopolymer has a molecular weight of from about 20,000 to about 40,000 daltons.

15. The composition as claimed in claim 14, wherein the polyethylene glycol homopolymer has a molecular weight of about 20,000 daltons.

16. The composition as claimed in claim 14, wherein the polyethylene glycol homopolymer has a molecular weight of about 30,000 daltons.

17. The composition as claimed in claim 16, wherein the human IL-18 substitution mutant has the amino acid sequence set forth in SEQ ID NO:4, and wherein the mutant is conjugated to the water-soluble polymer at the cysteine at residue 38.

18. The composition as claimed in claim 16, wherein the human IL-18 substitution mutant has the amino acid sequence set forth in SEQ ID NO:5, and wherein the mutant is conjugated to the water-soluble polymer at the cysteine at residue 78.

19. The composition as claimed in claim 16, wherein the human IL-18 substitution mutant has the amino acid sequence set forth in SEQ ID NQ:6, and wherein the mutant is conjugated to the water-soluble polymer at the cysteine at residue 121.

20. The composition as claimed in claim 16, wherein the human IL-18 substitution mutant has the amino acid sequence set forth in SEQ ID NO:7, and wherein the mutant is conjugated to the water-soluble polymer at the cysteine at residue 144.

21. The composition as claimed in claim 16, wherein the human IL-18 substitution mutant has the amino acid sequence set forth in SEQ ID NO:8, and wherein the mutant is conjugated to the water-soluble polymer at the cysteine at residue 157.

22. The composition as claimed in claim 16, wherein the human IL-18 substitution mutant has the amino acid sequence set forth in SEQ ID NO:9, and wherein the mutant is conjugated to the water-soluble polymer at the cysteine at residue 144.

23. The composition as claimed in claim 22, wherein the water-soluble polymer is chosen from the group of: linear polyethylene glycol homopolymer having a molecular weight of from about 20,000 to about 40,000 daltons and branched polyethylene glycol homopolymer having a molecular weight of from about 20,000 to about 40,000 daltons.

24. The composition as claimed in claim 23, wherein the linear polyethylene glycol homopolymer has a molecular weight of about 20,000 daltons.

25. The composition as claimed in claim 16, wherein the human IL-18 substitution mutant has the amino acid sequence set forth in SEQ ID NO:10, and wherein the mutant is conjugated to the water-soluble polymer at the cysteine at residue 157.

26. The composition as claimed in claim 25, wherein the water-soluble polymer is linear polyethylene glycol homopolymer having a molecular weight of from about 20,000 to about 40,000 daltons.

27. The composition as claimed in claim 26, wherein the linear polyethylene glycol homopolymer has a molecular weight of about 20,000 daltons.

28. The method as claimed in claim 25, wherein the water-soluble polymer is a polyethylene glycol homopolymer.

29. The composition as claimed in claim 14, wherein the polyethylene glycol homopolymer has a molecular weight of about 40,000 daltons.

30. A method of preparing a composition, said method comprising the steps of:
    (a) obtaining the human IL-18 substitution mutant polypeptide of SEQ ID NO:8; and
    (b) conjugating the polypeptide with a functionalized water-soluble polymer at the cysteine at residue 157.

31. The method of claim 30, wherein the functionalized water soluble polymer is a member chosen from the group of: methoxy polyethylene glycol succinimidyl propionate, MW 20,000; methoxy polyethylene glycol succinimidyl propionate, MW 30,000; methoxy polyethylene glycol succinimidyl butanoate, MW 20,000; succinimidyl ester of carboxymethylated methoxy polyethylene glycol, MW 20,000; methoxy polyethylene glycol aldehyde, MW 20,000; methoxy polyethylene glycol aldehyde, MW 30,000; methoxy polyethylene glycol hydrazide, MW 20,000; methoxy polyethylene glycol maleimide, MW 20,000; methoxy polyethylene glycol maleimide, MW 30,000; methoxy polyethylene glycol orthopyridyl disulfide, MW 20,000; methoxy polyethylene glycol orthopyridyl disulfide, MW 30,000; methoxy polyethylene glycol iodoacetamide, MW 20,000; and methoxy polyethylene glycol iodoacetamide, MW 30,000.

32. A method of improving the pharmacokinetics and pharmacodynamics of the human IL-18 substitution mutant of SEQ ID NO:8, said method comprising the step of conjugating the human IL-18 substitution mutant to a water-soluble polymer at the cysteine at residue 157.

33. The method as claimed in claim 32, wherein the subcutaneous bioavailability is improved.

34. The method as claimed in claim 32, wherein the subcutaneous bioavailability is improved, and binding to IL-8BP is reduced.

* * * * *